US012121258B2

(12) United States Patent
Stratton et al.

(10) Patent No.: US 12,121,258 B2
(45) Date of Patent: Oct. 22, 2024

(54) UNIVERSAL SCORING DEVICE

(71) Applicant: Surmodics, Inc., Eden Prairie, MN (US)

(72) Inventors: Derek Stratton, Eden Prairie, MN (US); John Bridgeman, Eden Prairie, MN (US)

(73) Assignee: Surmodics, Inc., Eden Prairie, MN (US)

( * ) Notice: Subject to any disclaimer, the term of this patent is extended or adjusted under 35 U.S.C. 154(b) by 56 days.

(21) Appl. No.: 17/128,138

(22) Filed: Dec. 20, 2020

(65) Prior Publication Data

US 2021/0212721 A1    Jul. 15, 2021

Related U.S. Application Data

(60) Provisional application No. 62/951,020, filed on Dec. 20, 2019, provisional application No. 62/951,971, filed on Dec. 20, 2019.

(51) Int. Cl.
*A61B 17/3207* (2006.01)
*A61B 17/00* (2006.01)
*A61M 25/10* (2013.01)

(52) U.S. Cl.
CPC ..... *A61B 17/320725* (2013.01); *A61M 25/10* (2013.01); *A61M 25/1011* (2013.01);
(Continued)

(58) Field of Classification Search
CPC .. A61B 17/320725; A61B 2017/00477; A61B 2017/00526; A61B 2017/00862;
(Continued)

(56) References Cited

U.S. PATENT DOCUMENTS 5,002,582 A    3/1991   Guire et al.
5,414,075 A    5/1995   Swan et al.
(Continued)

FOREIGN PATENT DOCUMENTS

EP       1556119        4/2014
JP       2015173913     10/2015
(Continued)

OTHER PUBLICATIONS

"International Application Serial No. PCT/US2019/032719, International Preliminary Report on Patentability mailed Nov. 26, 2020", 10 pgs.
(Continued)

*Primary Examiner* — Mohamed G Gabr
(74) *Attorney, Agent, or Firm* — Schwegman Lundberg & Woessner, P.A.

(57) ABSTRACT

In an example, a scoring device is configured for retention of a catheter shaft. The scoring device incudes a proximal portion and a distal portion. A retention sleeve extends between the proximal and distal portions. The retention sleeve has a catheter socket configured to selectively receive and mechanically engage the catheter shaft. The scoring device includes a scoring tool coupled with the retention sleeve, for instance proximate to the distal portion. The scoring tool includes a balloon socket configured to selectively receive a balloon of the catheter shaft. The scoring tool includes one or more scoring elements extending around the balloon socket, the one or more scoring elements configured to provide localized scoring to vasculature.

27 Claims, 21 Drawing Sheets

(52) U.S. Cl.
CPC ............... *A61B 2017/00477* (2013.01); *A61B 2017/00526* (2013.01); *A61B 2017/00862* (2013.01); *A61M 2025/1015* (2013.01); *A61M 2025/1081* (2013.01); *A61M 2205/0216* (2013.01); *A61M 2207/00* (2013.01)

(58) Field of Classification Search
CPC ............ A61B 2017/22061; A61M 2025/1015; A61M 2025/1081; A61M 2205/0216; A61M 2207/00; A61M 25/002; A61M 25/0113; A61M 25/10; A61M 25/1011; A61M 25/104

See application file for complete search history.

(56) References Cited

U.S. PATENT DOCUMENTS

| | | | |
|---|---|---|---|
| 5,637,460 A | 6/1997 | Swan et al. | |
| 5,647,848 A | 7/1997 | Slashed | |
| 5,752,934 A | 5/1998 | Campbell et al. | |
| 6,156,254 A | 12/2000 | Andrews et al. | |
| 6,167,605 B1 | 1/2001 | Morales | |
| 6,278,018 B1 | 9/2001 | Swan | |
| 6,616,678 B2 | 9/2003 | Nishtala et al. | |
| 6,904,743 B2 | 6/2005 | Vodinh | |
| 6,905,743 B1 | 6/2005 | Chen et al. | |
| 7,772,393 B2 | 9/2010 | Guire et al. | |
| 7,914,487 B2 | 3/2011 | Davies, Jr. et al. | |
| 8,002,741 B2 | 8/2011 | Hayes et al. | |
| 8,002,744 B2 | 8/2011 | Pepper et al. | |
| 8,105,275 B2 | 1/2012 | Pepper et al. | |
| 8,251,962 B2 | 8/2012 | Lenz | |
| 8,313,601 B2 | 11/2012 | Pepper et al. | |
| 8,323,546 B2 | 12/2012 | Hayes et al. | |
| 8,388,573 B1 | 3/2013 | Cox | |
| 8,394,055 B2 | 3/2013 | Durcan | |
| 8,864,704 B2 | 10/2014 | Beckham | |
| 9,149,612 B2 | 10/2015 | Chuter | |
| 9,179,936 B2 | 11/2015 | Feld et al. | |
| 9,211,391 B2 | 12/2015 | Davies, Jr. et al. | |
| 9,402,983 B1 | 8/2016 | Nath | |
| 9,440,055 B2 | 9/2016 | Simpson | |
| 9,629,945 B2 | 4/2017 | Kurdyumov et al. | |
| 9,631,190 B2 | 4/2017 | Mcgonigle | |
| 2001/0031981 A1* | 10/2001 | Evans ................... | A61B 17/221 606/200 |
| 2004/0073251 A1 | 4/2004 | Weber | |
| 2004/0243158 A1* | 12/2004 | Konstantino ......... | A61M 25/104 606/191 |
| 2005/0021071 A1 | 1/2005 | Konstantino et al. | |
| 2006/0015134 A1 | 1/2006 | Trinidad | |
| 2006/0085023 A1 | 4/2006 | Davies et al. | |
| 2006/0184191 A1 | 8/2006 | O'Brien | |
| 2006/0192054 A1 | 8/2006 | Lachenmeier | |
| 2006/0259005 A1* | 11/2006 | Konstantino ............ | A61P 9/10 623/1.42 |
| 2006/0271093 A1 | 11/2006 | Holman et al. | |
| 2007/0213761 A1 | 9/2007 | Murphy et al. | |
| 2008/0097301 A1 | 4/2008 | Alpini et al. | |
| 2008/0183132 A1 | 7/2008 | Davies et al. | |
| 2009/0038752 A1 | 2/2009 | Weng et al. | |
| 2009/0105687 A1 | 4/2009 | Deckman et al. | |
| 2009/0171284 A1 | 7/2009 | Burke et al. | |
| 2010/0023047 A1 | 1/2010 | Simpson | |
| 2010/0198168 A1 | 8/2010 | Rooijmans | |
| 2010/0274012 A1 | 10/2010 | Guire et al. | |
| 2011/0046255 A1 | 2/2011 | Rooijmans | |
| 2011/0059874 A1 | 3/2011 | Rooijmans et al. | |
| 2011/0144373 A1 | 6/2011 | Swan et al. | |
| 2011/0190867 A1 | 8/2011 | Vonderwalde et al. | |
| 2011/0245367 A1 | 10/2011 | Kurdyumov et al. | |
| 2011/0313506 A1 | 12/2011 | Ray et al. | |
| 2012/0149934 A1 | 6/2012 | Kurdyumov | |
| 2013/0087264 A1 | 4/2013 | Beckham | |
| 2013/0143056 A1 | 6/2013 | Swan et al. | |
| 2014/0277062 A1 | 9/2014 | Pepper et al. | |
| 2015/0133988 A1 | 5/2015 | Chuter | |
| 2017/0056061 A1* | 3/2017 | Ogle ..................... | A61B 17/221 |
| 2017/0065796 A1 | 3/2017 | Fojtik | |
| 2017/0105758 A1 | 4/2017 | Piccagli | |
| 2018/0036032 A1 | 2/2018 | Spencer et al. | |
| 2019/0351198 A1 | 11/2019 | Mullen et al. | |
| 2021/0330343 A1* | 10/2021 | Meerkin ............... | A61B 17/221 |

FOREIGN PATENT DOCUMENTS

| | | |
|---|---|---|
| WO | 2018008514 | 1/2018 |
| WO | WO-2019222536 A1 | 11/2019 |
| WO | WO-2019234659 A2 * | 12/2019 ........... A61B 17/221 |
| WO | 2021127609 | 6/2021 |

OTHER PUBLICATIONS

"International Application Serial No. PCT/US2019/032719, International Search Report mailed Jul. 18, 2019", 2 pgs.

"International Application Serial No. PCT/US2019/032719, Written Opinion mailed Jul. 18, 2019", 8 pgs.

"U.S. Appl. No. 16/414,597, Examiner Interview Summary mailed Jul. 14, 2023", 3 pgs.

"U.S. Appl. No. 16/414,597, Non Final Office Action mailed Aug. 17, 2023", 22 pgs.

"U.S. Appl. No. 16/414,597, Response filed Jul. 27, 2023 to Final Office Action mailed Mar. 27, 2023", 16 pgs.

"U.S. Appl. No. 16/414,597, Final Office Action mailed Feb. 9, 2024", 22 pgs.

"U.S. Appl. No. 16/414,597, Response filed Nov. 17, 2023 to Non Final Office Action mailed Aug. 17, 2023", 12 pgs.

"European Application Serial No. 20903837.1, Response filed Sep. 29, 2023 to Communication pursuant to Rule 70(2) and 70a(2) EPC mailed Apr. 4, 2023", 23 pgs.

"International Application Serial No. PCT US2020 066281, Invitation to Pay Additional Fees and Partial Search Report mailed Feb. 5, 2021", 2 pgs.

"U.S. Appl. No. 16/414,597, Non Final Office Action mailed Mar. 19, 2021", 24 pgs.

"European Application Serial No. 19803510.7, Response to Communication pursuant to Rules 161(2) and 162 EPC filed May 24, 2021", 17 pgs.

"International Application Serial No. PCT US2020 066281, International Search Report mailed Jun. 2, 2021", 3 pgs.

"International Application Serial No. PCT US2020 066281, Written Opinion mailed Jun. 2, 2021", 15 pgs.

"Emerge PTCA Dilation Catheter", Boston Scientific Corportation, (Aug. 2018), 5 pgs.

"Application Serial No. 16/414,597, Response filed Jun. 21, 2021 to Non Final Office Action mailed Mar. 19, 2021", 15 pgs.

"Application Serial No. 16/414,597, Final Office Action mailed Aug. 5, 2021", 25 pgs.

"Application Serial No. 16/414,597, Examiner Interview Summary mailed Nov. 22, 2021", 2 pgs.

"Application Serial No. 16/414,597, Response filed Dec. 3, 2021 to Final Office Action mailed Aug. 5, 2021", 13 pgs.

"Application Serial No. 16/414,597, Final Office Action mailed Jan. 3, 2022", 20 pgs.

"European Application Serial No. 19803510.7, Extended European Search Report mailed Feb. 9, 2022", 6 pgs.

"U.S. Appl. No. 16/414,597, Response filed Jun. 3, 2022 to Final Office Action mailed Jan. 3, 2022", 12 pgs.

"U.S. Appl. No. 16/414,597, Advisory Action mailed Jun. 30, 2022", 6 pgs.

"U.S. Appl. No. 16/414,597, Response filed Jun. 30, 2022 to Advisory Action mailed Jun. 30, 2022", 14 pgs.

"International Application Serial No. PCT US2020 066281, International Preliminary Report on Patentability mailed Jun. 30, 2022", 17 pgs.

"U.S. Appl. No. 16/414,597, Non Final Office Action mailed Aug. 23, 2022", 23 pgs.

(56) References Cited

OTHER PUBLICATIONS

"European Application Serial No. 19803510.7, Response filed Sep. 12, 2022 to Extended European Search Report mailed Feb. 9, 2022", 34 pgs.

"U.S. Appl. No. 16/414,597, Response filed Nov. 23, 2022 to Non Final Office Action mailed Aug. 23, 2022", 15 pgs.

"European Application Serial No. 20903837.1, Extended European Search Report mailed Mar. 15, 2023", 6 pgs.

"U.S. Appl. No. 16/414,597, Final Office Action mailed Mar. 27, 2023", 21 pgs.

"European Application Serial No. 19803510.7, Communication Pursuant to Article 94(3) EPC mailed May 6, 2024", 4 pgs.

"U.S. Appl. No. 16/414,597, Response filed Jul. 8, 2024 to Final Office Action mailed Feb. 9, 2024", 13 pgs.

\* cited by examiner

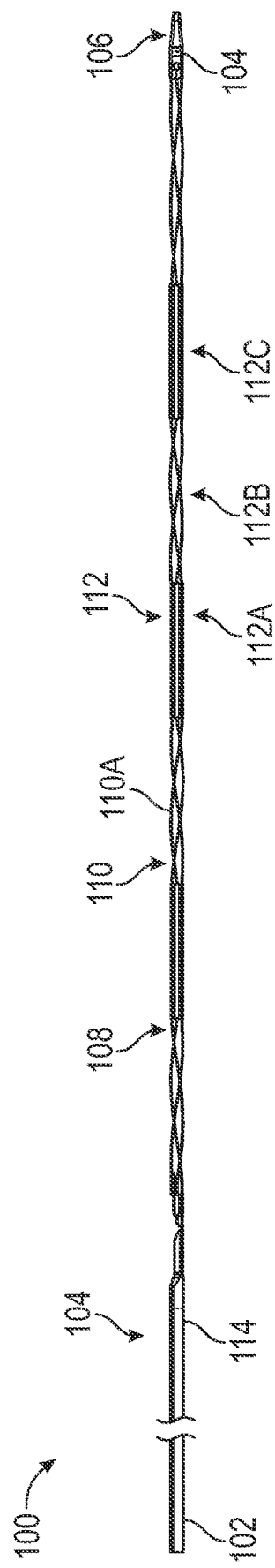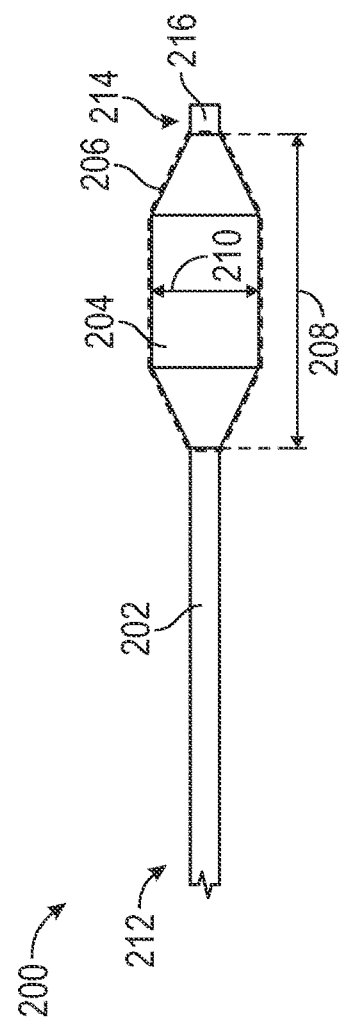

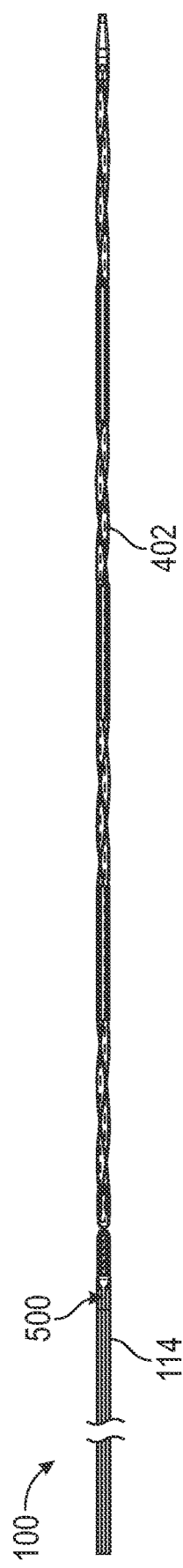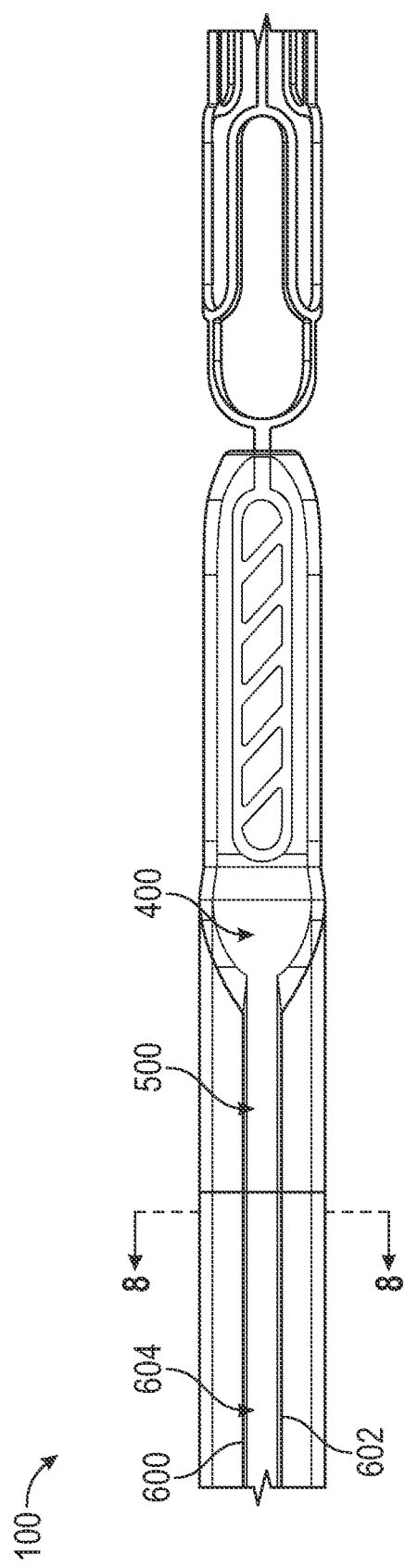
FIG. 5
FIG. 6

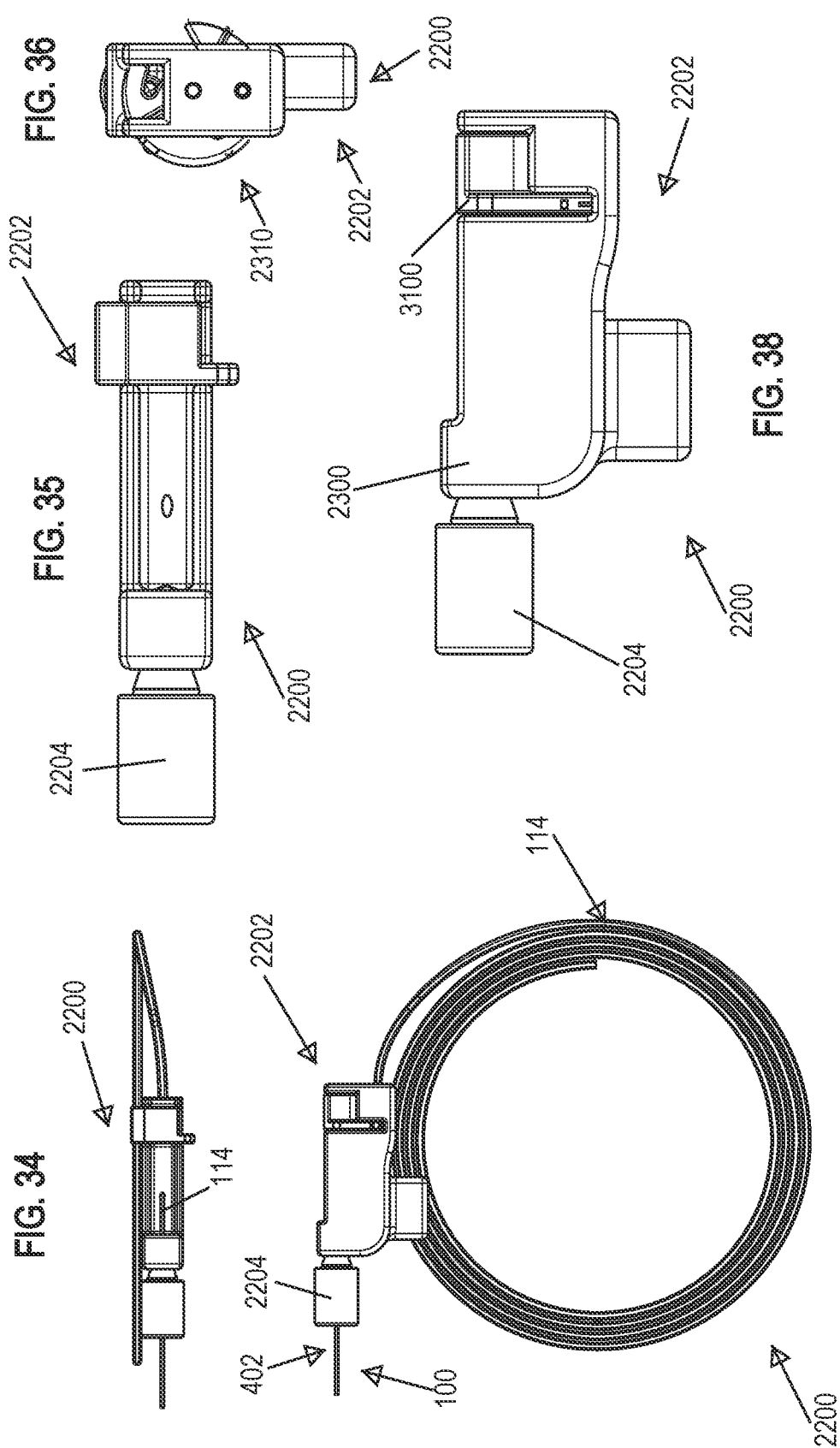

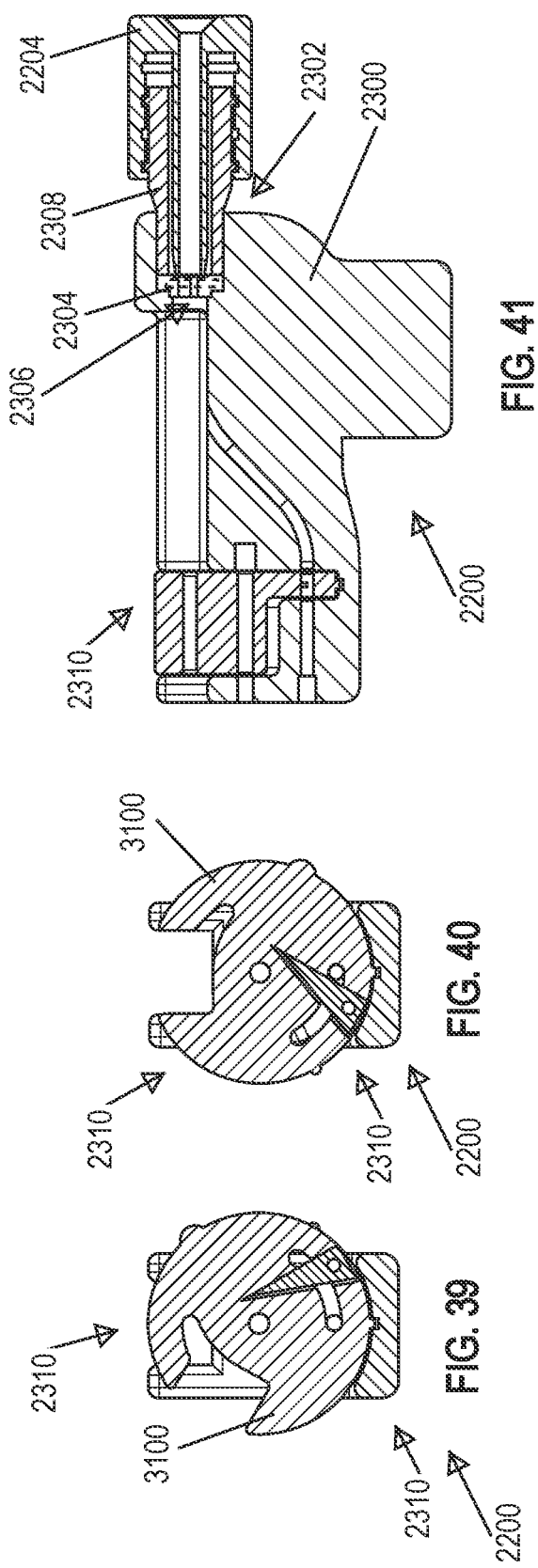
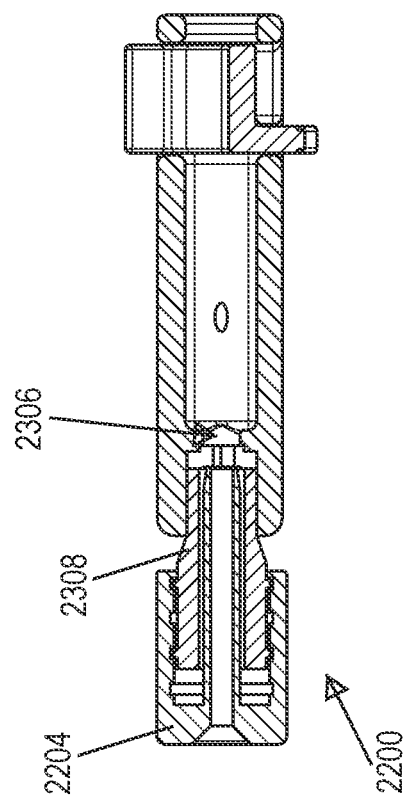
FIG. 39
FIG. 40
FIG. 41
FIG. 42

UNIVERSAL SCORING DEVICE

CLAIM OF PRIORITY

This patent application claims the benefit of priority of Stratton et al., U.S. Provisional Patent Application Ser. No. 62/951,020, entitled "UNIVERSAL SCORING DEVICE FOR BALLOON CATHETERS," filed on Dec. 20, 2019, and Stratton et al., U.S. Provisional Patent Application Ser. No. 62/951,971, entitled "UNIVERSAL SCORING DEVICE FOR BALLOON CATHETERS," filed on Dec. 20, 2019, the benefit of priority of each of which is claimed hereby, and each of which are incorporated by reference herein in its entirety.

TECHNICAL FIELD

This document pertains generally, but not by way of limitation, to a scoring device configured to receive a catheter.

BACKGROUND

In an approach, a catheter is coupled with a scoring device. The scoring device is bonded to a balloon of the catheter, and the scoring device is provided as a unitary assembly. Accordingly, in some approaches the catheter shaft is coupled (e.g., attached, glued, fused, or the like) with the catheter socket. Thus, each of the balloon, catheter, and cage have a specified size, or the like according to the particulars of the health care provider or application for the scoring device.

SUMMARY

The present inventors have recognized, among other things, that a problem to be solved can include attaching catheters of varying profiles to a scoring device. In some approaches, the scoring device is coupled to a corresponding cage. For instance, in an approach a balloon catheter having a specified length and balloon profile is coupled with a cage having a specified profile. Accordingly, the balloon catheter is not separable from the cage. However, variations in length of the catheter (and characteristics of the balloon) are optionally needed based on different medical procedures, vascular locations, patient-specific anatomical variations, or the like.

The present subject matter can help provide a solution to this problem, such as by a scoring device that is interchangeable with a plurality of catheters, each of the plurality of catheters optionally having a different profile. For instance, A single or limited number of the scoring devices is maintained on hand by a healthcare provider. The present subject matter allows a healthcare provider to retain a variety of catheters (with varying profiles) on hand for a variety of procedures, vessel locations or the like. Where scoring is specified to assist with treatment of vasculature, one or a limited number of scoring devices are ready for marriage with the plurality of catheters as needed. Thus, the present subject matter minimizes the number of unique catheters needed while at the same time providing enhanced flexibility of selection and marriage, for example by allowing the physician to select catheters as specified (e.g., from any number of brands, sizes or the like) and then marrying the selected catheter to the scoring device described herein.

In an example, the scoring device is configured to retain a catheter shaft. In an example, the scoring device includes a proximal portion and a distal portion. The distal portion includes a distal tip. The scoring device includes a retention sleeve extending between the proximal portion and the distal portion. The retention sleeve includes a catheter socket configured to selectively receive the catheter shaft. For instance, the catheter socket mechanically engages the catheter shaft while the catheter shaft is received in the catheter socket. Accordingly, the scoring device retains the catheter shaft within the catheter socket.

The catheter socket of the scoring device selectively receives the catheter shaft. In contrast, in some approaches the catheter shaft is affixed (e.g., attached, glued, fused, or the like) with the catheter socket and the catheter shaft is not separable from the catheter socket. As described herein, the selective reception of the catheter shaft by the catheter socket of the scoring device facilitates loading and separation of the catheter shaft from the scoring device. Thus, the catheter socket interchangeably receives one or more catheter shafts. For instance, the catheter socket interchangeably receives a first catheter shaft having a first profile, and a second catheter shaft having a second profile (different than the first profile). Accordingly, the scoring device interchangeably retains one or more catheter shafts. Thus, catheters of varying profiles are attached to the scoring device.

In another example, the scoring device includes a deformable catheter port. The deformable catheter port is elastically deformable, for example to receive the catheter shaft. For instance, the catheter socket may selectively receive the catheter shaft through the deformable catheter port. In an example, the catheter port extends between an exterior of the retention sleeve and the catheter socket. The catheter port receives catheter shafts of varying profiles (e.g., a first catheter shaft having a first size, and a second catheter shaft having a second size) because the catheter port is elastically deformable and the elastic deformation permits the catheter port (and the catheter socket) to receive and accommodate catheter shafts of varying profiles.

The scoring device includes a scoring tool. In an example, the scoring tool is coupled with the retention sleeve proximate to the distal portion. The scoring tool includes a balloon socket that selectively receives a balloon of the catheter shaft. The scoring tool includes one or more scoring elements. Optionally, the scoring elements are directed away from the balloon socket. The scoring elements provide localized scoring to vasculature when deployed with a loaded balloon that is inflated. For instance, the scoring elements mechanically deform plaque within a vein, for instance to facilitate removal of the plaque.

As described herein, the balloon socket selectively receives a balloon of the catheter shaft. In an example, the balloon includes a deflated configuration and an inflated configuration. The balloon is expandable (e.g., enlargeable, growable, dilatable, stretchable, or the like) between the deflated and inflated configurations. For example, in the inflated configuration, a volume of the balloon is larger than the volume of the balloon in the deflated configuration. The scoring tool expands outward in conformity with the balloon (with the balloon located in the balloon socket). For example, the scoring tool includes an initial configuration and an expanded configuration. In an example, expansion of the balloon (e.g., between the deflated and inflated configurations) facilitates transition of the scoring tool between the initial configuration and the expanded configuration. For instance, expansion of the balloon engages the balloon with the scoring tool and expands the scoring tool. As the balloon expands from the deflated configuration to the inflated configuration, the scoring tool expands in conformity with the balloon. Accordingly, in an example, transitioning of the balloon between deflated and inflated configurations correspondingly transitions the scoring tool between initial and expanded configurations.

In one example, the balloon socket selectively receives the balloon, for instance because the catheter is separate from the scoring device and loaded into the scoring device. For instance, the balloon socket selectively receives a balloon of a first catheter having a first profile. In an example, the first catheter includes a first catheter shaft having a first balloon, the first balloon having a first expanded volume. The first catheter is optionally interchanged with a second catheter, for instance by separating the first catheter from the scoring device. The second catheter has a second profile. For instance, the second catheter includes a second catheter shaft having a second balloon with a second expanded volume. The scoring device retains the second catheter shaft (e.g., with the retention sleeve selectively receiving and mechanically engaging the second catheter shaft), and the balloon socket selectively receives the second balloon. Accordingly, the scoring device is interchangeable with a plurality of catheters, each of the plurality of catheters optionally having a different profile.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 illustrates a side view of an example scoring device, according to an embodiment of the present subject matter.

FIG. 2 illustrates a side view of a catheter.

FIG. 5 illustrates a top view of the scoring device of FIG. 1, according to an embodiment of the present subject matter.

FIG. 6 illustrates a detailed top view of the scoring device of FIG. 1, according to an embodiment of the present subject matter.

FIG. 34 illustrates a top view of another example of a loading assembly, according to an embodiment of the present subject matter.

FIG. 35 illustrates a detailed top view of the loading assembly of FIG. 34, according to an embodiment of the present subject matter.

FIG. 36 illustrates an end view of the loading assembly of FIG. 34, according to an embodiment of the present subject matter.

FIG. 37 illustrates a side view of the loading assembly of FIG. 34, according to an embodiment of the present subject matter.

FIG. 38 illustrates a detailed side view of the loading assembly of FIG. 34, according to an embodiment of the present subject matter.

FIG. 39 illustrates a cross-sectional view of the loading assembly of FIG. 34, according to an embodiment of the present subject matter.

FIG. 40 illustrates another cross-sectional view of the loading assembly of FIG. 34, according to an embodiment of the present subject matter.

FIG. 41 illustrates yet another cross-sectional view of the loading assembly of FIG. 34, according to an embodiment of the present subject matter.

FIG. 42 illustrates still yet another cross-sectional view of the loading assembly of FIG. 34, according to an embodiment of the present subject matter.

DETAILED DESCRIPTION

Figure 3:
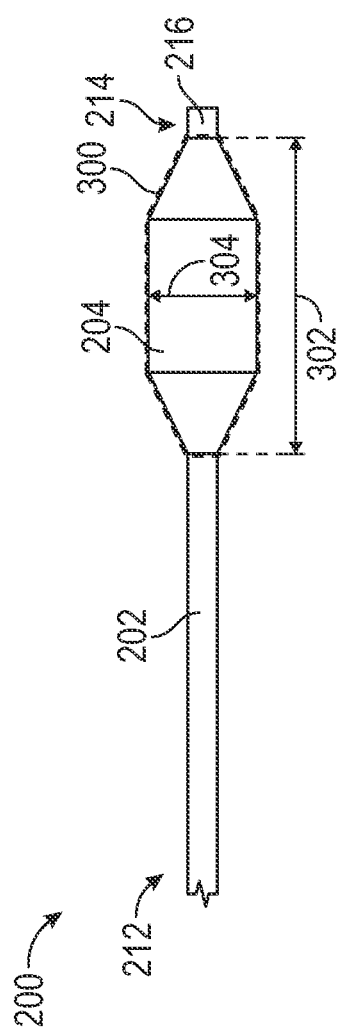
FIG. 3 illustrates another side view of the catheter of FIG. 2.

FIG. 1 illustrates a side view of an example scoring device 100. The scoring device 100 includes a proximal portion 102 and a distal portion 104. The distal portion 104 includes a distal tip 106. The scoring device 100 includes a scoring tool 108. For example, the scoring tool 108 is coupled proximate to the distal portion 104 of the scoring device 100.

The scoring tool 108 includes one or more scoring elements 110, for instance a first scoring element 110A. The one or more scoring elements 110 provide localized scoring (e.g., scraping, scratching, deforming, dislodging, cutting, shaving, parting, dividing, macerating, or the like) to vasculature. For instance, the scoring elements 110 facilitate removal of matter (such as plaque) from vasculature of a patient. In an example, the scoring elements 110 score the matter (e.g., plaque, or the like) to facilitate dilation of a vessel and the matter or, in another example, to facilitate separation of the matter from the vasculature. Accordingly, the scoring tool 108 facilitates dilation (e.g., compression), removal of matter from the vasculature by scoring the matter with the scoring elements 110.

In an example, the scoring tool 108 includes a plurality of sections 112. For example, the scoring tool 108 includes a first section 112A, a second section 112B, and a third section 112C. In some examples, and as described herein the sections 112 have different profiles from other sections 112. For example, the first section 112A includes a first scoring element profile (e.g., an elliptical profile, semicircular profile, elongate profile or the like) and the second section 112B includes a second scoring element profile (e.g., a helical profile, a screw profile, or the like).

The scoring device 100 includes a retention sleeve 114. The retention sleeve 114 extends between the proximal portion 102 and the distal portion 104. As described herein, the scoring device 100 retains a catheter shaft (e.g., the catheter shaft 202, shown in FIG. 2). For instance, the retention sleeve 114 includes a catheter socket (e.g., the catheter socket 400, shown in FIG. 4) that selectively receives and mechanically engages the catheter shaft to retain the catheter shaft in the retention sleeve 114 (and the scoring device 100). As described herein, the scoring device 100 is configured to interchangeably fit and couple with various catheters to provide flexibility by marrying the scoring device 100 with various catheters selected by a physician.

FIG. 2 shows an example of a catheter 200. In an example, the catheter 200 includes a catheter shaft 202 and a balloon 204. In an example, the balloon 204 extends from the catheter shaft 202. FIG. 2 shows the balloon in a deflated configuration. The balloon 204 is expandable between the deflated configuration and an inflated configuration (shown in FIG. 3). In the deflated configuration, the balloon 204 has a first balloon profile 206 (e.g., one or more of cross-section, shape, size, dimensions, contour, radius, perimeter, circumference, diameter, outline, boundary, configuration, pattern, arrangement, thickness, deployment from the catheter shaft 202, or the like). For instance, the balloon 204 has a first volume in the deflated configuration. In an example, the balloon 204 has a first characteristic 208 (e.g., length or the like). The balloon has a second characteristic 210 (e.g., a diameter, volume, cross-sectional area, shape, size, qualitative size relative to an inflated configuration or the like). In some examples, the first characteristic 208 and the second characteristic 210 provides the balloon 204 with the first balloon profile 206 (and the first volume).

The catheter 200 includes a proximal portion 212 and a distal portion 214. For example, the balloon 204 is included in the distal portion 214 of the catheter 200. In an example, the distal tip 106 of the scoring device 100 (shown in FIG. 1) receives the distal portion 214 of the catheter 200. For instance, the distal portion 214 of the catheter 200 includes distal coupling features 216, for example a balloon tip. In another example, the distal tip 106 of the scoring device 100 (shown in FIG. 1) receives the distal coupling features 216 of the catheter 200. In one example, the distal portion 214 (and the distal coupling features 216) is optionally seated in the distal tip 106 of the scoring device 100. In an example, seating of the distal coupling features 216 aligns the distal portion 214 of the catheter 200 relative to the distal portion 104 of the scoring device 100.

FIG. 3 shows another side view of the catheter 200 of FIG. 2. As described herein, the balloon 204 is expandable between the deflated configuration (shown in FIG. 2) and an inflated configuration (shown in FIG. 3). In the inflated configuration, the balloon 204 has a second balloon profile 300. In an example, the second balloon profile 300 is larger than the first balloon profile 206 (e.g., by volume, cross sectional area, size, shape, deployment from the catheter shaft 202 or the like). For instance, the balloon 204 has a second volume in the inflated configuration, and the second volume is larger than the first volume of the balloon 204 in the deflated configuration. In one example, in the inflated configuration, the balloon 204 has a third characteristic 302 (e.g., length), and the third characteristic 302 is larger than the first characteristic 208 (shown in FIG. 2). The balloon 204 has a fourth characteristic 304 (e.g., diameter, volume, cross-sectional area, shape, size, qualitative size relative to a deflated configuration or the like) in the inflated configuration. The fourth characteristic 304 is larger than the second characteristic 204. In some examples, the third characteristic 302 and the fourth characteristic 304 provides the balloon 204 with the second balloon profile 206 (and the second volume). Accordingly, a transition of the balloon 204 between the deflated and inflated configurations correspondingly transitions the balloon 204 between having the first balloon profile 206 (shown in FIG. 2) and having the second balloon profile 300 (shown in FIG. 3). Thus, the volume of the balloon 204 transitions between the first volume in the deflated configuration, and the second volume in the inflated configuration. In an example, a change in volume of the balloon 204 includes one or more of a change in length, height, width, cross-sectional area, or the like of the balloon 204.

Figure 4:
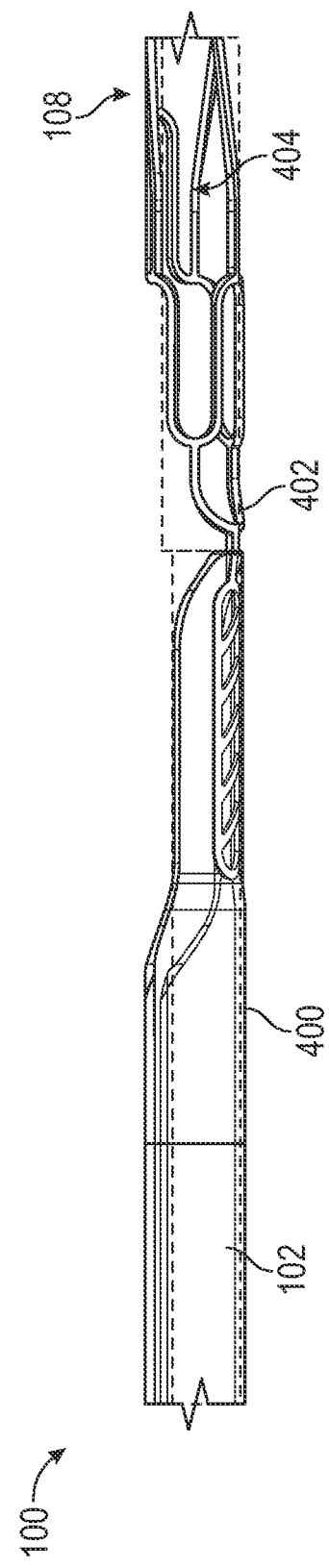
FIG. 4 illustrates a detailed side view of the scoring device of FIG. 1, according to an embodiment of the present subject matter.

FIG. 4 illustrates a detailed side view of the scoring device 100 of FIG. 1, according to an embodiment of the present subject matter. As described herein, the scoring device 100 includes the retention sleeve 114. In an example, the retention sleeve 114 facilitates retention of a catheter shaft (e.g., the catheter shaft 202, shown in FIG. 2) by the scoring device 100.

In an example, the retention sleeve 114 includes a catheter socket 400. The catheter socket 400 is configured to receive a catheter shaft, for instance the catheter shaft 202 (shown in FIG. 2). The catheter socket 400 mechanically engages the catheter shaft, for example when the catheter shaft is received in the catheter socket 400. In another example, the catheter socket 400 grasps the catheter shaft to facilitate retention of the catheter shaft by the retention sleeve 114 (e.g., during loading, use of the assembly or the like).

As described herein, the scoring device 100 includes the scoring tool 108. In an example, the scoring tool 108 includes a balloon socket 402. The balloon socket 402 selectively receives a balloon, for instance the balloon 204 (shown in FIG. 2). The scoring elements 110 surround the balloon socket 402, and with the balloon 204 loaded into the scoring device 100, the scoring elements 110 surround the balloon including continuously and discontinuously. In another example, the scoring elements 110 are directed away from the balloon socket 402. For example, the scoring elements 110 include a scoring edge 404. In one example, the scoring edge 404 of the scoring elements 110 is directed away from the balloon socket 402, for instance to minimize engagement of the scoring edge 404 with the balloon 204. In another example, the balloon socket is located on a first side (e.g., an interior side, or the like) of the scoring element 110, and the scoring edge 404 is located on a second side (e.g., an exterior side, opposed side or the like) of the scoring element 110. Optionally, the scoring edge 404 is located remotely relative to the balloon socket 402 to minimize interaction with the balloon 204.

FIG. 5 illustrates a top view of the scoring device 100 of FIG. 1, according to an embodiment of the present subject matter. As described herein, the scoring tool 108 includes the catheter socket 400 (shown in FIG. 4). The catheter 200 includes a catheter port 500 that provides access to the catheter socket 400, for instance through the retention sleeve 114. The catheter port 500 is in communication with the catheter socket 400. In an example, the catheter port 500 is elastically deformable, for instance to facilitate ingress (or egress) of the catheter shaft into (our out of) the catheter socket 400. As further shown in FIG. 5, in this example the catheter port 500 of the scoring device includes an elongate slot extending through the retention sleeve 114. The retention sleeve 114 is deformable and biases the port 500 (e.g., the slot) toward a closed configuration that captures a loaded catheter shaft within the catheter socket 400. As described herein, a loading assembly biases the port 500 open, for instance with biasing of a catheter shaft, to initiate loading of the catheter shaft to the catheter socket 400 and continue loading through the port 500 (e.g., a slot) along the retention sleeve 114.

FIG. 6 illustrates a detailed top view of the scoring device 100 of FIG. 1, including the interface between the retention sleeve and the scoring tool 108. As described herein, the scoring device 100 includes the catheter port 500, and the catheter port 500 is in communication with the catheter socket 400. In an example, the catheter port 500 facilitates selective reception of a catheter shaft by the retention sleeve 114. For instance, the catheter port 500 (e.g., the retention sleeve 114 forming the port) is elastically deformable to facilitate ingress (or egress) of the catheter shaft into (or out of) the catheter socket 400. In one example, the catheter port 500 includes a first face 600 and a second face 602 (also shown in FIG. 8). The first face 600 is opposed to the second face 602. The first face 600 and the second face 602 extend between the proximal portion 102 and the distal portion 104. A slot 604 is optionally located between the opposed first and second faces 600, 602. In one example, the catheter port 500 is the slot 604 extending at least a portion of the length of the retention sleeve 114 (e.g., between the proximal and distal portions).

Elastic deformation of the catheter port 500 varies a size of port 500, for instance by changing spacing between the first face 600 and the second face 602. In this example, because the catheter port 500 is elastically deformable, the catheter port 500 is configured to receive a variety of catheter shafts having different profiles (e.g., diameters, cross sectional areas or the like). Accordingly, the catheter port 500 facilitates interchangeable reception of catheter shafts having varying profiles. For instance, elastic deformation of the catheter port 500 allows the catheter socket 400 to interchangeably receive a first catheter shaft having a first profile, a second catheter shaft having a different second profile or the like. Thus, catheter shafts are interchangeably received in the catheter socket 400 and loaded and unloaded through the catheter port 500 (and deformation of the port).

Figure 7:
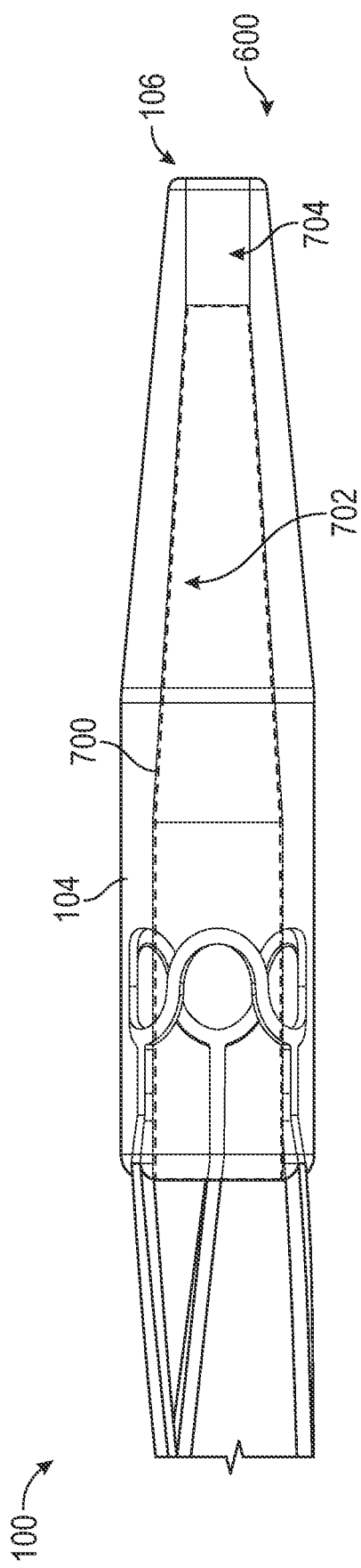
FIG. 7 illustrates a side view of a distal portion of the scoring device of FIG. 1, according to an embodiment of the present subject matter.

FIG. 7 illustrates a side view of the distal portion 104 of the scoring device 100 of FIG. 1, according to an embodiment of the present subject matter. In an example, the distal portion 104 includes the distal tip 106. In another example, the distal portion 104 of the scoring device 100 includes a distal tip socket 700. The distal tip socket 700 receives a portion of a catheter, for instance the catheter 200 (shown in FIG. 2). In one example, the distal portion 214 of the catheter 200 (shown in FIG. 2) is optionally seated in the distal tip socket 700 of the scoring device 100.

As discussed herein, the catheter 200 includes the distal coupling features 216 (shown in FIG. 2). In an example, the distal tip socket 700 receives the distal coupling features 216. For instance, the distal tip socket 700 includes a tapered portion 702 that receives the distal coupling features 216 of the catheter 200. In another example, the tapered portion 702 that receives the distal coupling features 216 aligns the distal portion 214 of the catheter 200 relative to the distal tip socket 700. Further, in some examples, the distal coupling features 216 are seated in the tapered portion 702, for example with an interference fit, with complementary profiles or the like between the distal coupling features 216 and the tapered portion 702. Accordingly, the distal portion 214 of the catheter 200 is optionally seated in the distal tip socket 700.

Figure 8:
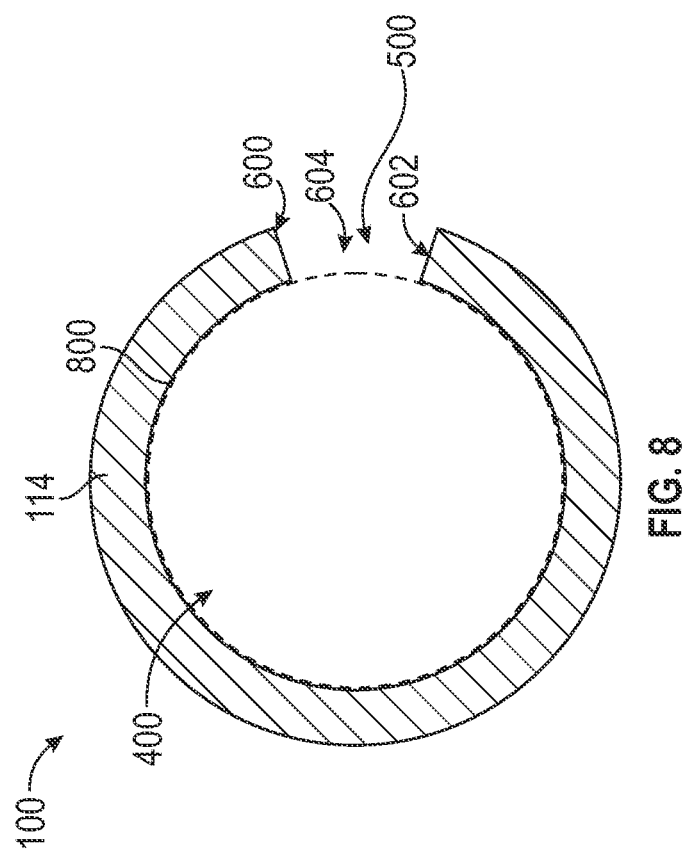
FIG. 8 illustrates a cross-sectional view of the scoring device of FIG. 6 at the line 8-8, according to an embodiment of the present subject matter.

FIG. 8 illustrates a cross-sectional view of the scoring device 100 of FIG. 6 at the line 8-8, according to an embodiment of the present subject matter. As described herein, the retention sleeve 114 includes the first face 600 opposed to the second face 602. For example, the retention sleeve 114 extends arcuately from the first face 600 to the second face 602. Optionally, the retention sleeve 114 has an arcuate cross section interrupted with the catheter port 500. In another example, the catheter port 500 is located between the first face 600 and the second face 602. In some examples, the catheter port 500 includes the slot 604 (e.g., an elongate slot, or the like), and the slot 604 extends along the first face 600 and the second face 602. In one example, elastic deformation of the retention sleeve 114 varies the size of the port 500 (or slot 604), for instance by changing spacing between the first face 600 and the second face 602. The catheter port 500 is in communication with the catheter socket 400, and the catheter port 500 facilitates ingress (or egress) of a catheter shaft into (or out of) the catheter socket 400. Additionally, as described herein the bias provided by the retention sleeve 114 facilitates retention of the catheter shaft within the catheter socket 400 during loading and use of the assembled device (e.g., catheter and scoring device). For instance, the retention sleeve 114 biases the catheter port 500 (or slot 604) toward the initial position shown in FIG. 8, and accordingly grasps and retains the catheter shaft therein.

FIG. 8 shows the catheter socket 400 has a first socket profile 800 (e.g., one or more of length, cross-section, shape, size, dimensions, contour, radius, perimeter, circumference, diameter, outline, boundary, configuration, pattern, arrangement, thickness or the like). As described herein, the socket profile 800 varies with elastic deformation of the retention sleeve 114. For instance, the socket profile 800 is varied to change a volume of the catheter socket 400 and thereby accommodate various catheter shafts.

Figure 9:
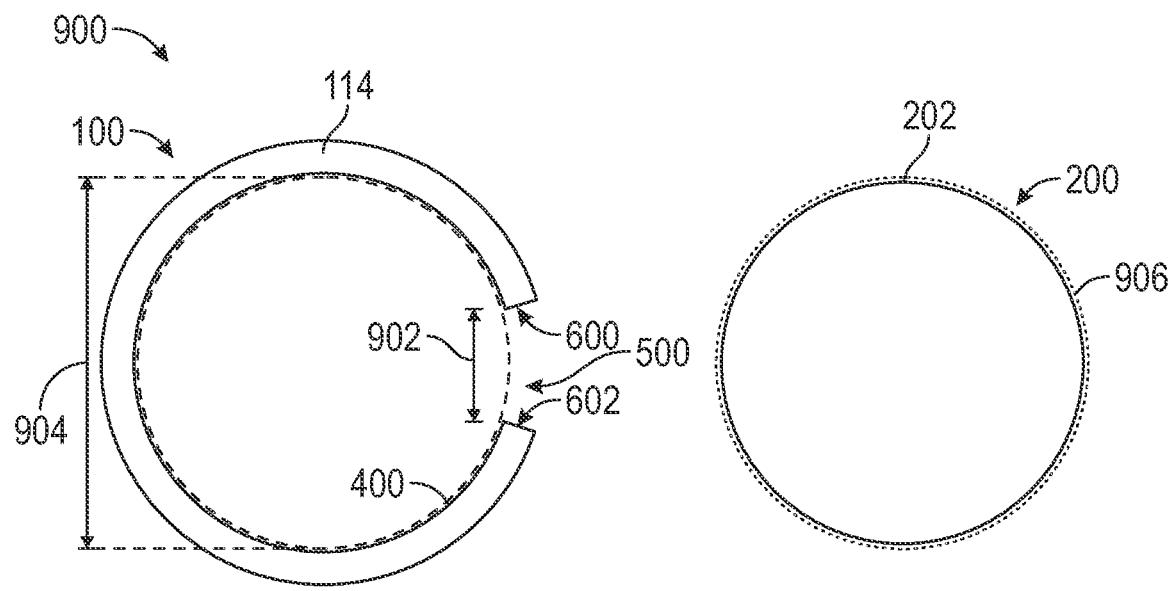
FIG. 9 illustrates a side view of a scoring tool, according to an embodiment of the present subject matter.

FIG. 9 illustrates an example of catheter assembly 900, according to an embodiment of the present subject matter. In an example, the catheter assembly 900 includes the scoring device 100 and the catheter 200. As described herein, the scoring device 100 retains a catheter shaft, for instance the catheter shaft 202. For example, the catheter socket 400 selectively receives the catheter shaft 202 through the catheter port 500. In another example, the retention sleeve 114 is elastically deformable to facilitate reception of the catheter shaft 202.

For example, FIG. 9 shows the retention sleeve 114 in an initial configuration. In the initial configuration, the catheter socket 400 has the first socket profile 800. Elastic deformation of the catheter port 500 facilitates reception of the catheter shaft 202 by the catheter socket 400. For example, in the initial configuration, the first face 600 is proximate the second face 602. Optionally, elastic deformation separates the first face 600 from the second face 602, for instance to vary a characteristic 902 of the catheter port 500.

Further, FIG. 9 shows the catheter shaft 202 of the catheter 200 having a first shaft profile 906. In an example, elastic deformation of the retention sleeve 114 allows the socket profile 800 to correspond with the shaft profile 906. Accordingly, the retention sleeve 114 mechanically engages the catheter shaft 202, for instance when the catheter shaft is selectively received by the catheter socket 400. For example, the mechanical engagement of the catheter socket 400 with the catheter shaft 202 constrains relative movement between the catheter shaft 202 and the retention sleeve 114. In one example, the mechanical engagement constrains rotational movement of the catheter shaft 202 about a longitudinal axis of the retention sleeve 114. In another example, the mechanical engagement constrains lateral movement of the catheter shaft along the longitudinal axis of the retention sleeve 114. In yet another example, the retention sleeve 114 grasps the catheter shaft 202 to facilitate the catheter socket 400 mechanically engaging the catheter shaft 202. The retention sleeve 114 accordingly joins the scoring device 100 with the catheter 200 and consolidates the separate devices (scoring device 100 and catheter 200) in a unitary assembly for use by the physician.

Figure 10:
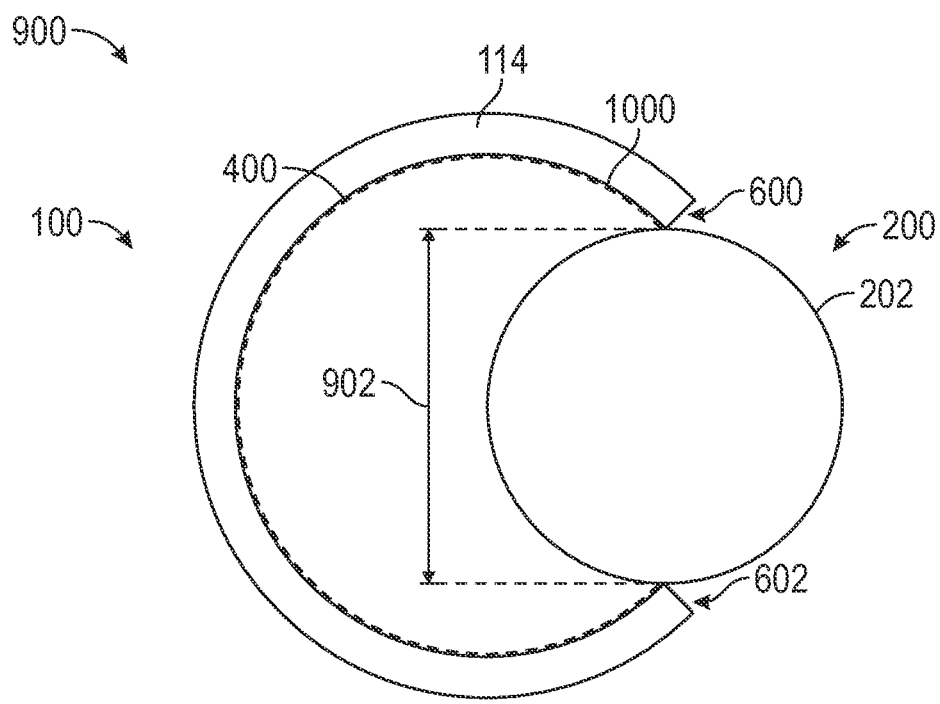
FIG. 10 illustrates another example of the catheter assembly of FIG. 9, according to an embodiment of the present subject matter.

FIG. 10 illustrates another example of the catheter assembly 900 of FIG. 9, according to an embodiment of the present subject matter. As described herein, the retention sleeve 114 is elastically deformable. For instance, the retention sleeve includes a loading configuration, and in loading configuration the retention sleeve is elastically deformed relative to the initial configuration (shown in FIG. 9). In an example, in the loading configuration the first face 600 and the second face 602 are biased apart (and the retention sleeve 114 is correspondingly deformed) relative to the initial configuration (shown in FIG. 9, where the first face 600 is proximate the second face 602). Accordingly, the profile of the catheter socket 400 is varied from the first socket profile 800 (shown in FIG. 9) to a second socket profile 1000.

For instance, a user (e.g., a technician, healthcare worker, physician or the like) engages (e.g., presses, pushes, squeezes, or the like and optionally using a loading device described herein) the catheter shaft 202 with the first and second faces 600, 602 to separate the first face 600 from the second face 602. Accordingly, the elastically deformed retention sleeve 114 having the catheter port 500 facilitates reception of the catheter shaft 202 through the catheter port 500. Thus, FIG. 10 shows the retention sleeve 114 in a loading configuration, and the catheter shaft 202 is at least partially located within the catheter socket 400 (e.g., the catheter shaft at least partially intersects the catheter socket 400).

As described herein, elastic deformation of the retention sleeve 114 varies a profile of the catheter socket 400. For instance, FIG. 10 shows the retention sleeve 114 in the loading configuration, and the catheter socket 400 has a second socket profile 1000. In an example, the second socket profile 1000 (shown in FIG. 10) is larger than the first socket profile 800 (shown in FIG. 9) because of the elastic deformation of the retention sleeve 114.

Figure 11:
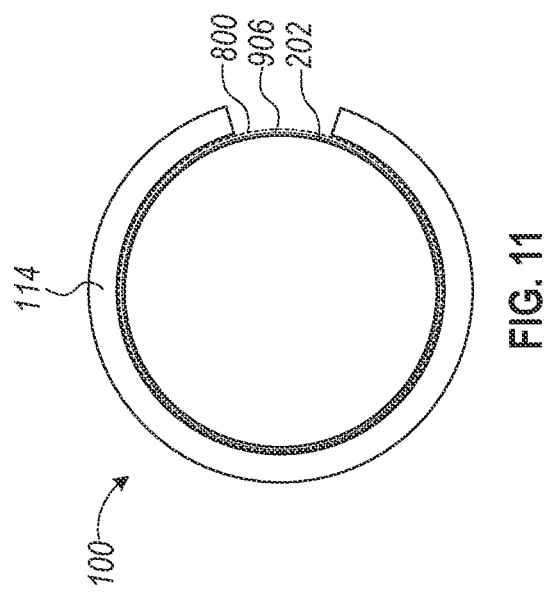
FIG. 11 illustrates yet another example of the catheter assembly of FIG. 9, according to an embodiment of the present subject matter.

FIG. 11 illustrates yet another example of the catheter assembly 900 of FIG. 9, according to an embodiment of the present subject matter. FIG. 11 shows the catheter shaft 202 selectively received (e.g., loaded) within the catheter socket 400 of the retention sleeve 114. For instance, the first socket profile 800 corresponds with the first shaft profile 906. Accordingly, the catheter socket 400 mechanically engages the catheter shaft 202, and the catheter shaft 202 is retained by the scoring device 100.

Figure 12:
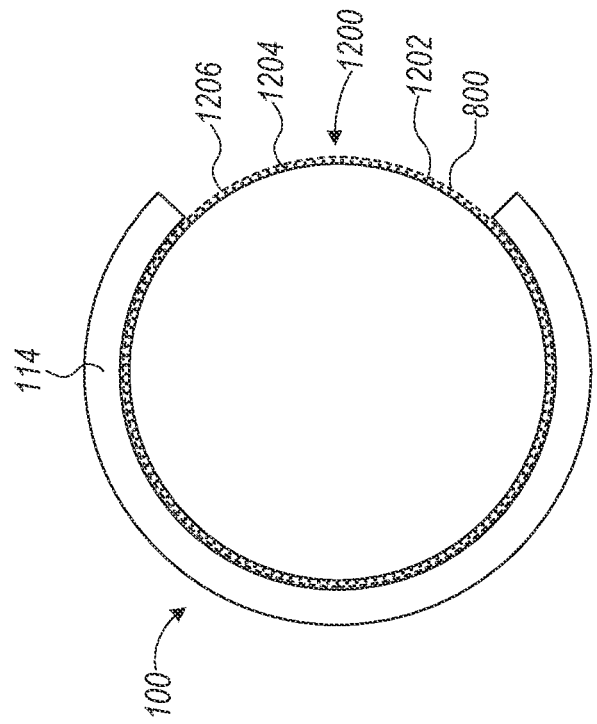
FIG. 12 illustrates still yet another example of the catheter assembly of FIG. 9, according to an embodiment of the present subject matter.

FIG. 12 illustrates still yet another example of the catheter assembly 900 of FIG. 9, according to an embodiment of the present subject matter. In an example, the catheter assembly 900 includes a second catheter 1200 having a second catheter shaft 1202. The second catheter shaft 120 has a second shaft profile 1204 larger than the first shaft profile 906 (shown in FIG. 11). For example, a diameter of the second catheter shaft 1202 is larger than a diameter of the first catheter shaft 202. In another example, the second catheter shaft 1202 is longer than the first catheter shaft 202. In yet another example, the catheter shaft 1202 is longer and has a larger diameter than the first catheter shaft 202.

Referring to FIG. 12, the socket profile 800 corresponds to the shaft profile 1204. The socket profile 800 corresponds with the shaft profile 1204 because the retention sleeve 114 is elastically deformable. The elastic deformation of the retention sleeve 114 enlarges the socket profile 800 and allows the catheter socket 400 (shown in FIG. 8) to interchangeably receive catheters (or portions of catheters) having varied profiles. Accordingly, the scoring device 100 retains catheters with varying profiles, for example the first catheter 200 with the first shaft profile 906 (shown in FIG. 11) or the second catheter 1200 with the second shaft profile 1204 (shown in FIG. 12).

Figure 13:
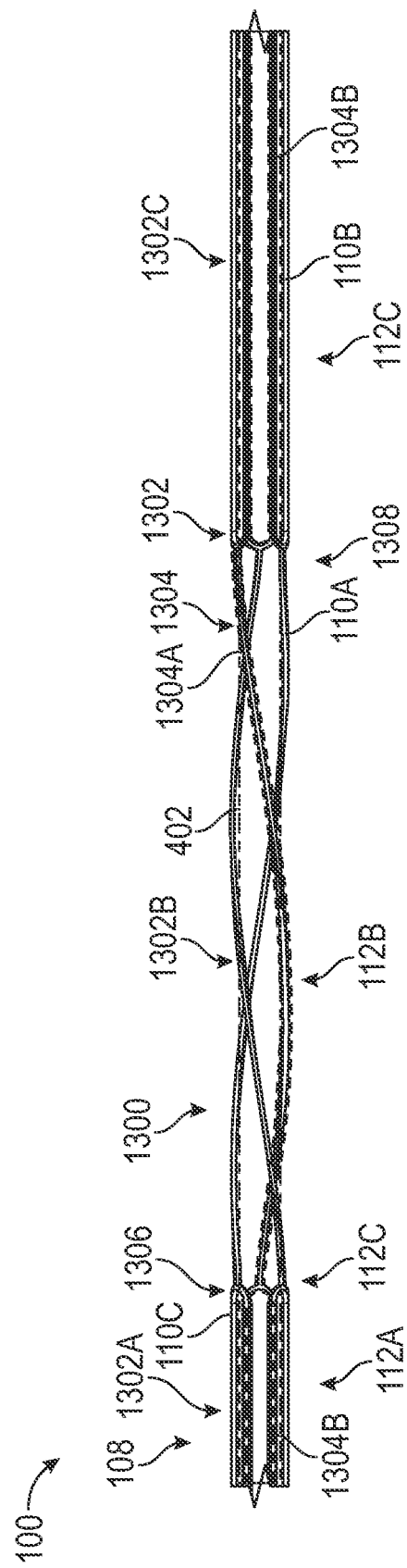
FIG. 13 illustrates a side view of a scoring tool, according to an embodiment of the present subject matter.

FIG. 13 illustrates a side view of the scoring tool 108 of the scoring device 100, according to an embodiment of the present subject matter. The scoring device 100 includes the scoring tool 108 extending between proximal and distal portions 102, 104 (shown in FIG. 1). The scoring tool 108 includes the sections 112, such as the sections 112A, 112B, 112C. The scoring tool 108 includes one or more scoring elements 110, for example the first scoring element 110A and a second scoring element 110B. In an example, two or more of scoring elements 110 (e.g., elements 110A, 110B) are included in a scoring array 1300. For example, the scoring array 1300 includes scoring elements with varying scoring element profiles 1304. In one example, the first section 112A of the scoring tool 108 includes a first scoring section 1302A, as shown having a longitudinally extending configuration of scoring elements. The second section 112B of the scoring tool 108 includes a second scoring section 1302B, for instance a helical configuration of scoring elements. The second scoring section 1302B has a first scoring element profile 1304A (e.g., helical profile, elliptical profile, semicircular profile, or the like). For instance, the second scoring section 1302B includes the first scoring element 110A, and the first scoring element 110A has the first scoring element profile 1304A. The third section 112C of the scoring tool 108 includes a third scoring section 1302C. The third scoring section 1302C has a second scoring element profile 1304B (e.g., an elongate profile or the like). For example, the third scoring section includes the second scoring element 110B, and the second scoring element 110B has the second scoring element profile 1304B similar or identical to the profile 1304B of the first scoring section 1302A.

Referring to FIG. 13, the first scoring element 110A is optionally coupled with the second scoring element 110B. In another example, the first scoring section 112A includes a third scoring element 110C, and the third scoring element 110C is coupled with the first scoring element 110A. For instance, a first end 1306 of the first scoring element 110A is coupled with the third scoring element 110C. A second end 1308 of the first scoring element 110A is coupled with the second scoring element 110B. Accordingly, the scoring section 1302B extends between the scoring sections 1302A and the scoring section 1302C.

Figure 14:
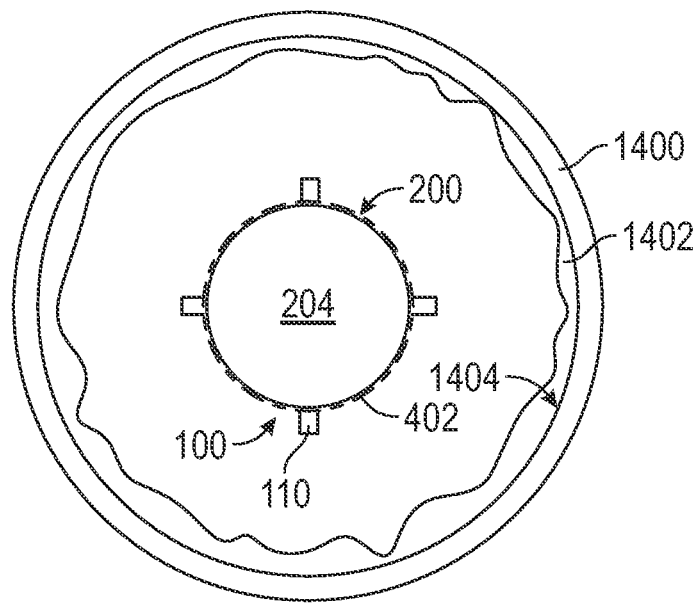
FIG. 14 illustrates a catheter retained by the scoring device of FIG. 1, according to an embodiment of the present subject matter.

FIG. 14 illustrates the catheter 200 retained by the scoring device 100, according to an embodiment of the present subject matter. For instance, the balloon 204 of the catheter 200 is loaded within the balloon socket 402 (also shown in FIGS. 4 and 5), and the scoring device 100 retains the catheter 200 therein (e.g., with the retention sleeve 114). The scoring device 100 including the scoring elements 110 (and the catheter 200 including the balloon 204) are navigated through the vasculature 1400, for instance a vein, artery, or the like. In some approaches, matter such as plaque 1402 is adhered (e.g., bound, stuck, attached, compacted, or the like) to the vasculature 1400, for instance to a wall 1404 of the vasculature 1400. As described herein, the balloon 204 and the scoring tool of the scoring device 100 are provided in a compressed or deflated configuration and the balloon 204 is inflated to an expanded or inflated configuration that also deploys the scoring tool 108. FIG. 14 shows the balloon 204 in the deflated configuration (also shown in FIG. 2).

Figure 15:
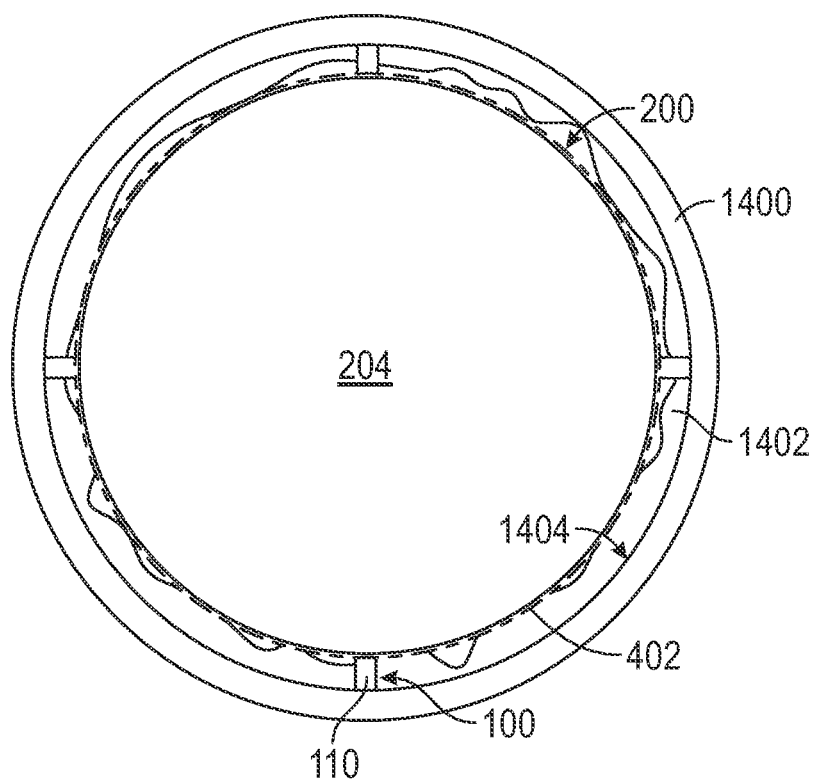
FIG. 15 illustrates another example of the catheter of FIG. 2 retained by the scoring device of FIG. 1, according to an embodiment of the present subject matter.

FIG. 15 illustrates another example of the catheter 200 retained by the scoring device 100, according to an embodiment of the present subject matter. FIG. 15 shows the balloon 204 in the inflated configuration (also shown in FIG. 3) and shows the scoring tool 108 in an expanded configuration conforming to inflation of the balloon 204. For example, the balloon 204 is enlarged to engage the scoring elements 110 with one or more of the vasculature 1400 or the plaque 1402 adhered to the vasculature 1400. Accordingly, the scoring tool 108 facilitates scoring of the plaque 1402. The balloon 204 and the scoring tool 108 work in concert to dilate the vessel. In one example, the scoring tool 108 separates or subdivides the plaque 1402 to facilitate dilation of the plaque 1402 with the inflated balloon 204. Thus, the scoring tool 108 enhances treatment of plaque 1402 from the vasculature 1400 including, but not limited to, dilation of vessels (compression of plaque 1402), removal of plaque or the like.

Figure 16:
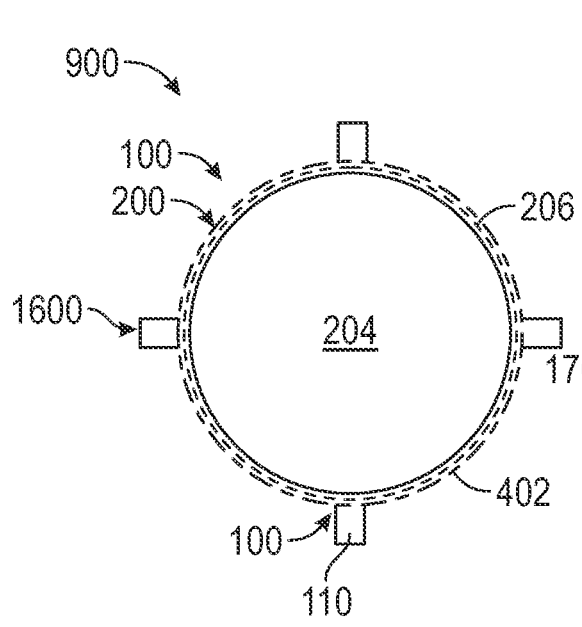
FIG. 16 illustrates an example of the catheter assembly with the catheter of FIG. 2 and the scoring device, according to an embodiment of the present subject matter.

FIG. 16 illustrates an example of the catheter assembly 900 with the first catheter 200 and the scoring device 100, according to an embodiment of the present subject matter. FIG. 16 shows the balloon 204 in the deflated configuration and with the first balloon profile 206. In an example, the balloon 204 of the catheter 200 is selectively received in the balloon socket 402 of the scoring device 100 and the scoring device 100 retains the catheter 200 therein (e.g., with the retention sleeve 114). For instance, the scoring elements 110 are directed away from the balloon 202 selectively received in the balloon socket 402.

Referring to FIG. 16, the scoring tool includes an initial configuration and an expanded configuration. In the initial configuration, the scoring tool has a first tool profile 1600. For instance, the balloon 204 is selectively received in the balloon socket 402 with the balloon 204 in the deflated configuration.

Figure 17:
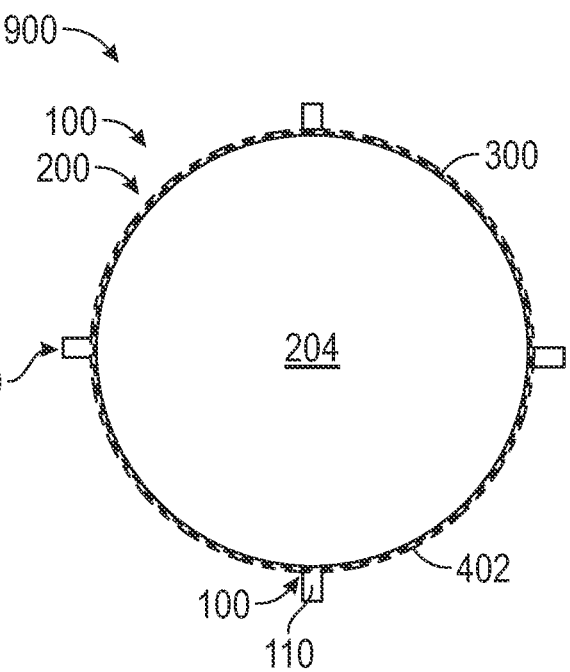
FIG. 17 illustrates another example of the catheter assembly with the catheter of FIG. 2 and the scoring device, according to an embodiment of the present subject matter.

FIG. 17 illustrates another example of the catheter assembly 900 with the first catheter 200 and the scoring device 100, according to an embodiment of the present subject matter. FIG. 17 shows the balloon 204 in the inflated configuration and with the second balloon profile 300. The balloon 204 and the scoring tool 108 work in concert to dilate the vessel. In one example, the scoring tool 108 separates or subdivides matter (such as plaque) to facilitate dilation of the matter with the inflated balloon 204. In an example, the scoring tool 108 expands outward in conformity with the expansion of the balloon 204 to the inflated configuration. In another example, the scoring tool 108 accommodates the balloon 204 transitioning between the deflated and inflated configurations. For instance, the expansion of the balloon 204 radially displaces the scoring elements 110. Thus, the scoring tool 108 has a second tool profile 1700 with the balloon 204 in the inflated configuration (and having the second balloon profile 300). The second tool profile 1700 is larger than the first tool profile 1600. For example, the scoring elements 110 are radially displaced to increase spacing between the scoring elements 110 (in comparison to the initial configuration) and provide the scoring tool 108 with the second tool profile 1700. Accordingly, the balloon socket 402 selectively receives the balloon 204 with varying balloon profiles (e.g., one or more of the balloon profiles 206, 300).

Figure 18:
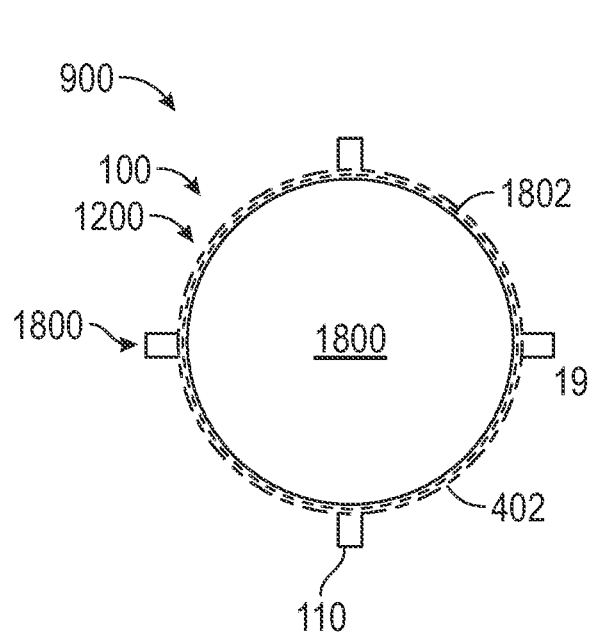
FIG. 18 illustrates an example of the catheter assembly with another example of a catheter and the scoring device 100, according to an embodiment of the present subject matter.

FIG. 18 illustrates an example of the catheter assembly 900 with the second catheter 1200 and the scoring device 100, according to an embodiment of the present subject matter. The second catheter 1200 includes a second balloon 1800 that includes deflated and inflated configurations. The balloon 1800 has a third balloon profile 1802 in the deflated configuration. For example, the third balloon profile 1802 includes a first initial volume for the second balloon 1800. Referring to FIG. 16, the first balloon profile 206 includes a second initial volume for the first balloon 1800. In an example, the first balloon profile 1802 is smaller than the third balloon profile 1802. Thus, the scoring tool 108 has a third tool profile 1804 with the balloon 1800 in the deflated configuration (and having the third balloon profile 1802). The third tool profile 1804 is optionally, larger than the first tool profile 1600.

FIG. 18 shows the balloon 204 in the deflated configuration and with the first balloon profile 206. In an example, the balloon 204 of the catheter 200 is selectively received in the balloon socket 402 of the scoring device 100. Accordingly, the balloon socket 402 selectively receives the balloons, for instance the balloon 204 or the balloon 1800 with varying balloon profiles (e.g., one or more of the balloon profiles 206, 300, 1802).

Figure 19:
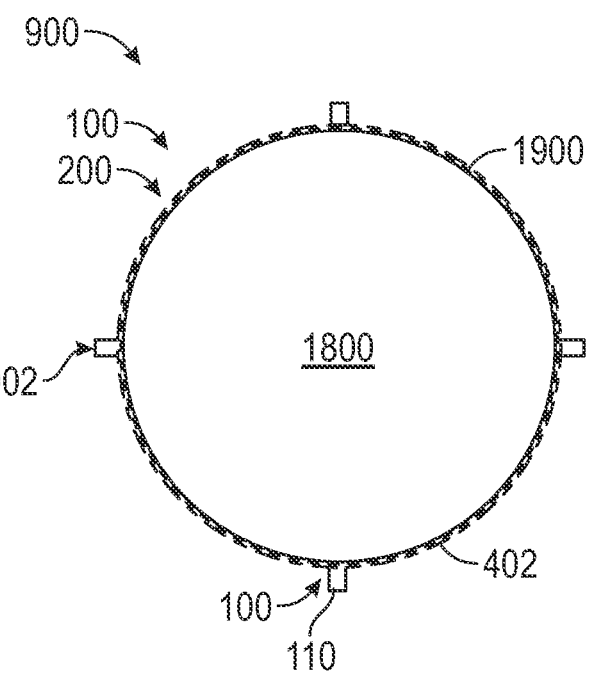
FIG. 19 illustrates another example of the catheter assembly with another example of a catheter and the scoring device 100, according to an embodiment of the present subject matter.

FIG. 19 illustrates another example of the catheter assembly 900 with the second catheter 1200 and the scoring device 100, according to an embodiment of the present subject matter. FIG. 19 shows the balloon 1800 in the inflated configuration with a fourth balloon profile 1900. In an example, the scoring tool 108 expands outward in conformity with the expansion of the balloon 1800 (or the balloon 204, shown in FIGS. 16-17) to the inflated configuration. In another example, the scoring tool 108 accommodates the balloon 1800 transitioning between the deflated and inflated configurations. Thus, the scoring tool 108 has a fourth tool profile 1902 with the balloon 1800 in the inflated configuration (and having the fourth balloon profile 1900). The fourth tool profile 1900 is larger than the third tool profile 1804. For example, the scoring elements 110 are radially displaced to increase spacing between the scoring elements 110 (in comparison to the initial configuration) and provide the scoring tool 108 with the fourth tool profile 1902. Accordingly, the balloon socket 402 selectively receives the balloon 1800 (or the balloon 204) with varying balloon profiles (e.g., one or more of the balloon profiles 206, 300, 1802, 1900).

Figure 20:
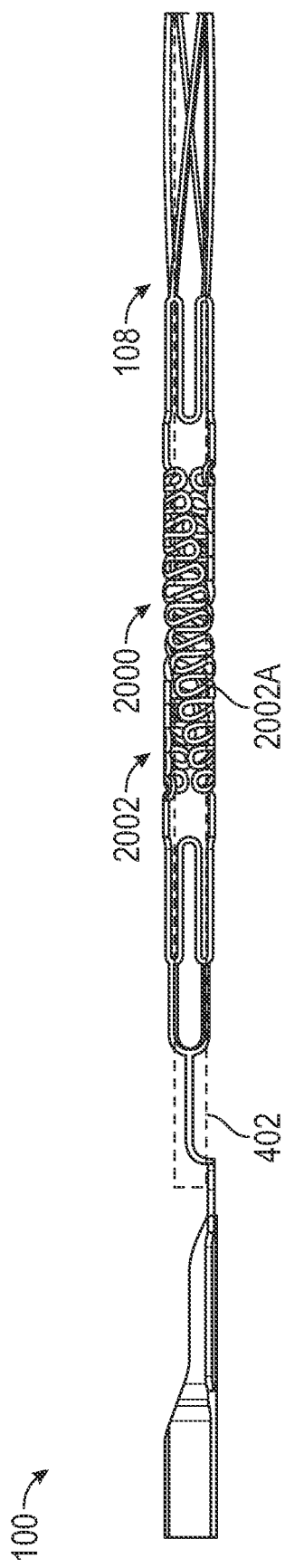
FIG. 20 illustrates a side view of another example of the scoring device, according to an embodiment of the present subject matter.
Figure 21:
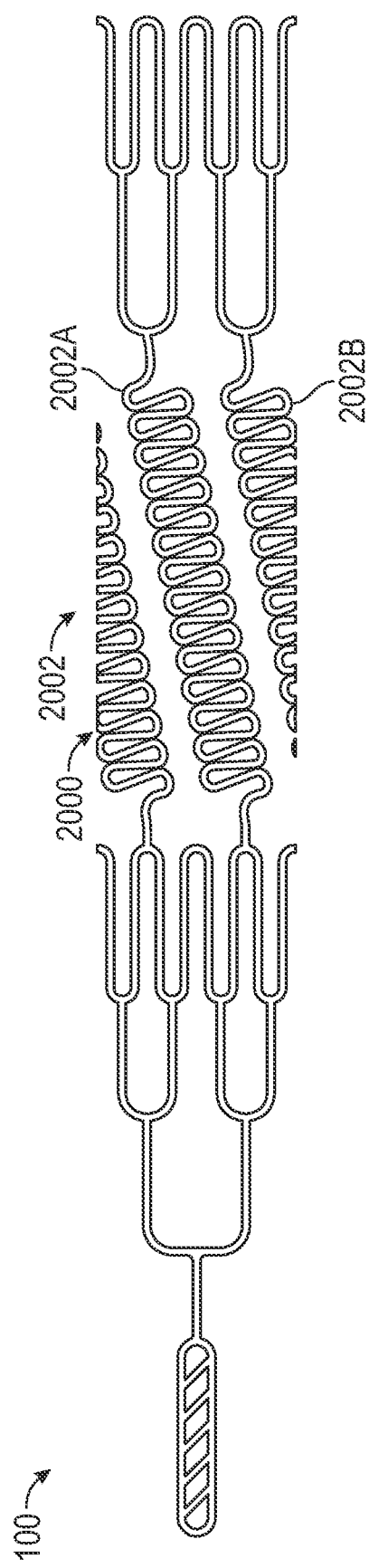
FIG. 21 illustrate a plan view of the scoring device of FIG. 20, according to an embodiment of the present subject matter.

FIGS. 20 and 21 illustrate side and detailed plan views (respectively) of another example of the scoring device 100, according to an embodiment of the present subject matter. In an example, the scoring device 100 includes at least one longitudinal expansion region 2000. As shown in this example, the longitudinal expansion region 2000 includes one or more expansion ribbons 2002 that elastically deform and facilitate expansion of the scoring tool 108 (e.g., expansion from the initial configuration to the expanded configuration). The expansion ribbons 2002 in one example include a serpentine or concertina configuration that facilitates elastic expansion and contraction that maintains the scoring tool 108 in conformance with the balloon in both inflated and deflated configurations and intermediate configurations therebetween. Additionally, as described herein the expansion ribbons 2002 permit inflation of a balloon received in the balloon socket of the scoring tool 108 while minimizing interference of inflation that may affect the specified inflation configuration of the balloon (e.g., by binding, anchoring or the like with struts or features that fail to expand).

In one example, the expansion ribbons 2002 facilitate one or more of axial or radial expansion of the scoring tool 108. The expansion of the scoring tool 108 from the initial configuration to the expanded configuration in some examples axially expands and radially expands the scoring tool. For instance, the radius of the balloon perimeter relative to the catheter shaft enlarges through inflation of the balloon. The scoring tool 108 shown in FIGS. 20 and 21 expands to accommodate the enlargement. Because the radius of the balloon increases during expansion and the scoring tool 108 is coupled along the balloon, the scoring tool follows the increase in radius (at both ends of the balloon) and thereby lengthens with the expansion ribbons 2002 to accommodate the change in balloon radius while minimizing interference with balloon inflation.

In an example, the expansion ribbons 2002 are isolated from proximate expansion ribbons 2002. For example, the scoring tool 108 includes a first ribbon 2002A isolated from a second ribbon 2002B. Instead, the first and second ribbons 2002A, B separately extend between scoring elements or other components of the scoring tool 108. In another example, the first ribbon 2002A is not directly coupled with the second ribbon 2002B. Accordingly, the first ribbon 2002A is allowed to expand axially independently of the axial expansion of the ribbon 2002B. Thus, axial expansion of the scoring tool 108 is enhanced, for instance because the first ribbon 2002A does not bind with the second ribbon 2002B while the scoring tool transitions between initial and expanded configurations. Additionally, each of the ribbons 2002 independently conforms to changes in the balloon during inflation without interference from proximate ribbons 2002.

In another example, the ribbons 2002 extend helically around the balloon socket 402. Helically winding the ribbons 2002 around the balloon socket 402 minimizes sagging or separation of the scoring tool 108 from a balloon (e.g., the balloon 1800, shown in FIG. 18) selectively received within the balloon socket 402. Accordingly, retention and engagement of the scoring tool 108 to the loaded balloon is enhanced with helical wrapping of the balloon socket (and the balloon therein) with the ribbons 2002. Additionally, performance of the scoring device 100 is enhanced, because the scoring tool 108 mechanically engages the balloon in each of the deflated and inflated configurations (and intermediate configurations) and helical winding of the ribbons 2002 around the balloon socket 402 enhances the mechanical engagement between the scoring tool 108 and the balloon and thereby facilitates enhanced conformance of the scoring tool 108 to the profile of the balloon.

Figure 22:
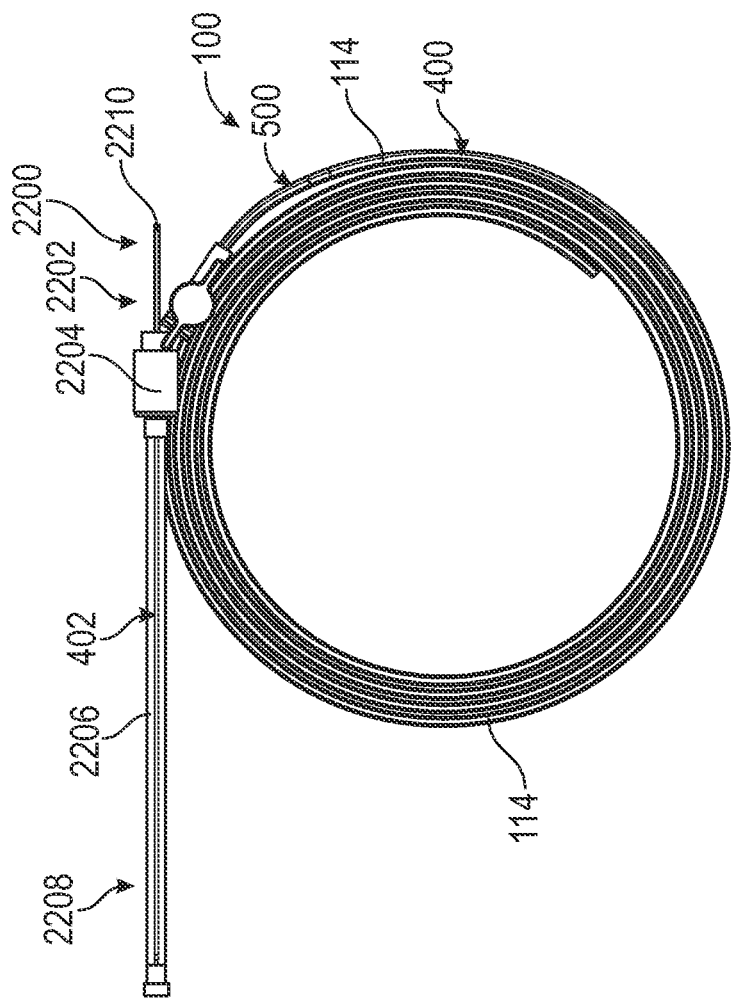
FIG. 22 illustrates an example of a loading assembly, according to an embodiment of the present subject matter.

FIG. 22 illustrates an example of a loading assembly 2200, according to an embodiment of the present subject matter. For instance, the loading assembly 2200 includes an assembly tool 2202 that facilitates assembly of a catheter assembly, for example the catheter assembly 900 (shown in FIG. 9), having the scoring device 100 described herein and one or more catheters (e.g., balloon catheters). In an example, the assembly tool 2202 facilitates assembly of the scoring device 100 to a catheter, for instance the catheter 200 (shown in FIG. 2) or the catheter 1200 (shown in FIG. 12). For example, the assembly tool 2202 facilitates elastic deformation of the catheter port 500 (shown in FIG. 5) and ingress of the catheter 200 into the catheter socket 400 of the scoring device 100. Accordingly, the assembly tool 2202 facilitates reception of a balloon within the balloon socket of the scoring device 100, opening of the scoring device 100, and loading of the catheter shaft into the retention sleeve for retention of the shaft therein. Thus, the assembly tool 2202 facilitates assembly of the scoring device 100 with a plurality of catheters, each of the catheters having different profiles.

In an example, the assembly tool 2202 includes an assembly interface 2204. The assembly interface 2204 receives each of the retention sleeve 114 and the catheter 200 in separated or partially separated conditions. For instance, the assembly interface 2204 facilitates assembly of the retention sleeve 114 over the catheter shaft 202.

In an example, the loading assembly 2200 includes a scoring tool sheath 2206 coupled with the assembly tool 2202. For instance, the scoring tool sheath 2206 surrounds and protects the scoring tool 108 of the scoring device 100. The scoring tool sheath 2206 extends between the assembly interface 2204 and a distal portion of the loading assembly 220.

In another example, the loading assembly 2200 includes a catheter loading mandrel 2210. The catheter loading mandrel 2210 facilitates alignment of components of the loading assembly 2200. For instance, the mandrel 2210 facilitates axial alignment of the scoring device 100 with the catheter 200. The catheter loading mandrel 2210 is optionally coupled with the scoring tool sheath 2206. For example, the catheter loading mandrel 2210 extends through the assembly tool 2202 (and the assembly interface 2204) from an opposed end of the scoring tool sheath 2206. Optionally, the catheter loading mandrel 2210 extends through one or more of the catheter socket 400 of the retention sleeve 114 or the balloon socket 402 of the scoring tool 108. For instance, the catheter loading mandrel 2210 extends between the proximal and distal portions 102, 104 of the scoring device 100 and is within the catheter and balloon sockets 400, 402 of the scoring device. In some examples, the distal tip socket 700 of the scoring device passes the catheter loading mandrel 2210 through the balloon socket 402. The mandrel 2210 optionally extends through the distal tip socket 700, for example through the mandrel lumen 704 of the distal portion 104 of the scoring device 100. Accordingly, the mandrel 2210 extends through one or more components of the loading assembly 2200 to facilitate alignment (and assembly) of the scoring device 100 and the catheter 200.

Figure 23:
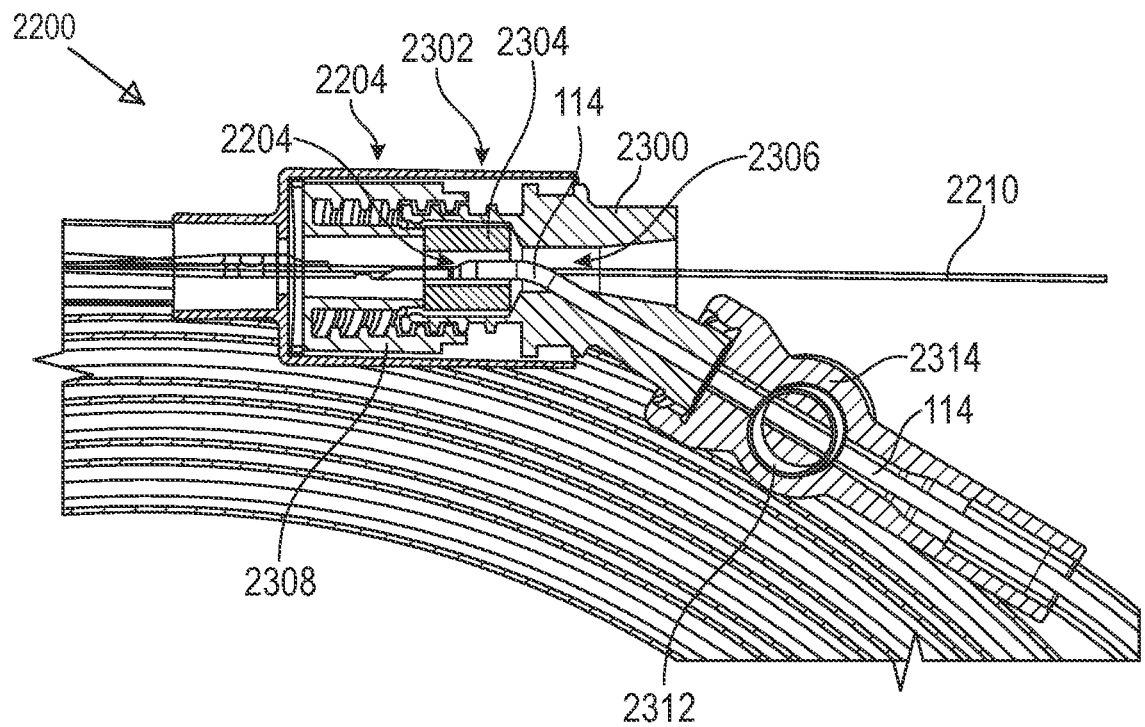
FIG. 23 illustrates a cross-sectional view the loading assembly including the assembly interface, according to an embodiment of the present subject matter.

FIG. 23 illustrates a cross-sectional view the loading assembly 2200 including the assembly interface 2204, according to an embodiment of the present subject matter. In an example, the assembly interface 2204 includes a loading interface 2300 and an assembly fitting 2302. The loading interface 2300 facilitates assembly of the catheter assembly 900, for example by aligning the retention sleeve 114 with the mandrel 2210. In one example, the mandrel 2210 is at least partially received in the catheter socket 400. In an example, the mandrel 2210 elastically deforms the catheter port 500 and the retention sleeve to facilitate ingress of the catheter shaft 202 into the catheter socket 400. Thus, the mandrel 2210 facilitates assembly of the catheter assembly 900 by assisting in the elastic deformation of the retention sleeve. Accordingly, the mandrel 2210 facilitates the catheter socket 400 selectively receiving the catheter shaft 202 by elastically deforming the retention sleeve 114 and aligning the catheter 200 relative to the scoring device 100. In another example, the catheter loading mandrel 2210 guides the balloon (e.g., the balloon 204) of the catheter through the assembly tool 2202 and into the balloon socket 402 of the scoring tool 108.

As described herein, the assembly interface 2204 includes the assembly fitting 2302. The assembly fitting 2302 facilitates assembly of the retention sleeve 114 over the catheter 200. For instance, the assembly fitting 2302 receives each of the retention sleeve 114 and the catheter 200, with the sleeve 114 and the catheter 200 in a decoupled configuration. In an example, the decoupled configuration includes the catheter shaft 202 separate from the catheter socket 400 of the scoring device 100. In another example, the balloon of the catheter is received within the balloon socket 402 of the scoring tool 108. For instance, the mandrel 2210 guides the balloon (e.g., the balloon 204) of the catheter through the assembly tool 2202 and into the balloon socket 402 of the scoring tool 108.

In another example, the mandrel 2210 and the loading interface 2300 cooperate to align the retention sleeve 114 relative to the catheter shaft 202. The assembly fitting 2302 receives each of the retention sleeve 114 and the catheter 200 (for instance the catheter shaft 202) and assembles the retention sleeve over the catheter 200 to provide an assembled configuration to the catheter assembly 900.

In an example, the assembly fitting 2302 is a collet 2304 that extends around the retention sleeve 114 and the catheter 200. For instance, the assembly collet 2304 is compressible (e.g., elastomeric, squeezable, shrinkable, squishable, or the like) to assemble the retention sleeve 114 over the balloon catheter 200. In another example, the assembly fitting 2302 biases the retention sleeve 114 over the catheter 200. For instance, the assembly fitting 2302 opens an elongate slot (e.g., the slot 604, shown in FIG. 6) through radial compression around each of the retention sleeve and the catheter 200. The compression biases the catheter 200 through the catheter port 500 of the retention sleeve (e.g., an elongate slot extending along the retention sleeve). In yet another example, opening the elongate slot facilitates reception of the catheter 200 within the retention sleeve 114 because elastic deformation of the retention sleeve 114 allows ingress (or egress) of the catheter shaft 202 into the catheter socket 400. Thus, the assembly fitting 2302 facilitates loading of the catheter 200 to the scoring device 100 by driving the catheter 200 through the catheter port 500 and into the catheter socket of the retention sleeve 114.

In another example, the assembly fitting 2302 is forced (e.g., pushed, extruded, compressed, pulled, drawn, or the like) through the loading interface 2300, for instance to compress the assembly fitting 2302 (and assemble the scoring device 100 with the catheter 200). For instance, the assembly interface 2204 is rotatably coupled relative to the assembly collet 2304. In one example, the assembly interface 2204 is rotatably coupled with the loading interface 2300. The assembly fitting 2302 is received in the loading interface 2300, and rotation of the assembly interface 2204 compresses the assembly fitting 2302 with the loading interface 2300. For example, the assembly collet 2304 is forced through a compression orifice 2306 of the loading interface 2300. The compression orifice 2306 includes a constriction (e.g., reduction in cross-sectional area, or the like) within the loading interface 2300, and forcing of the collet 2304 through the orifice 2306 compresses the assembly collet 2304. For instance, the collet 2304 is deformable, and compression of the collet 2304 deforms the collet 2304 to engage the collet 2304 with components received therein (e.g., one or more of the retention sleeve 114, the catheter, or the mandrel 2210, or the like). In an example, the loading assembly evenly applies a force across the catheter assembly as the collet 2304 is forced through the orifice 2306 (e.g., the collet 2304 is compressed concentrically around a perimeter of the collet 2304). In another example, assembly fitting 2302 clamps the retention sleeve 114 to the catheter 200, for instance by compressing the collet 2304 with one or more components of the catheter 200 located in the collet 2304. Accordingly, the clamping of the retention sleeve to the catheter 200 minimizes separation of the retention sleeve 114 from the catheter 200.

As discussed herein, rotation of the assembly interface 2204 compresses the assembly fitting 2302. For instance, the loading assembly 2200 includes an assembly drive 2308, and rotation of the assembly interface 2204 displaces the assembly drive 2308 relative to the loading interface 2300. The assembly interface 2204 (and the assembly drive 2308) are rotatably coupled with the assembly fitting 2302, and in an example, the displacement of the assembly drive 2308 compresses the assembly collet 2304 by engaging with the collet 2304 to force the collet 2304 through the compression orifice 2306 of the loading interface 2300. For instance, a barrel of the assembly drive 2308 engages with the assembly fitting 2204 (in this example the collet 2304). Optionally, the barrel of the assembly drive 2308 is received by a corresponding barrel socket of the loading interface 2300. Accordingly, the assembly fitting 2302 transitions the retention sleeve 114 and the catheter from the decoupled configuration to the assembled configuration. Thus, the loading assembly 2200 facilitates biasing of the retention sleeve 114 over the catheter to assemble the catheter assembly 900 (shown in FIG. 11).

Referring to FIG. 23, in an example the loading assembly 2200 includes a cutter 2310. For instance, the cutter 2310 includes a sleeve cutting element 2312 received in a sleeve cutting housing 2314. In an example, the sleeve cutting housing 2314 is coupled with the assembly tool 2202, for instance coupled with the loading interface 2300. In another example, the sleeve cutting element 2312 is positioned along the retention sleeve 114, and the retention sleeve 114 passes through the sleeve cutting element 2312. As described herein, the catheter assembly 900 includes a decoupled configuration and an assembled configuration. In the decoupled configuration, the retention sleeve 114 passes through a cutting orifice (e.g., the cutting orifice 3200, shown in FIG. 32) of the sleeve cutting element 2312. A user engages with the cutter 2310, for instance to rotate the sleeve cutting element 2312 relative to the sleeve cutting housing 2314. In an example, rotation of the sleeve cutting element 2312 severs the retention sleeve 114. For instance, the sleeve cutting element 2312 proximate the cutting orifice engages with the retention sleeve 114 to sever (e.g., cut, slice, chop, shear, or the like) the retention sleeve 114. Thus, in the assembled configuration, the sleeve cutting element severs the retention sleeve 114, for instance to trim the retention sleeve 114 to a specified length (e.g., to a retention sleeve length corresponding to a length of a catheter shaft). Accordingly, the retention sleeve 114 is severed proximate the catheter, for example to facilitate marriage of the retention sleeve 114 with the catheter.

Figure 24:
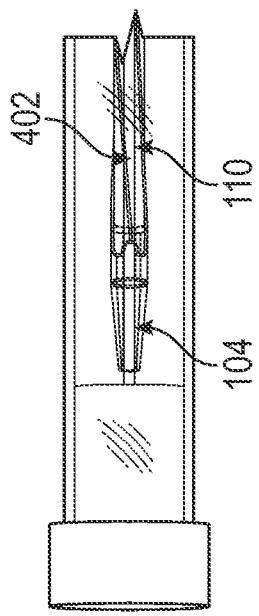
FIG. 24 illustrates a detailed side view of a distal portion of the loading assembly, according to an embodiment of the present subject matter.

FIG. 24 illustrates a detailed side view of the distal portion 2208 of the loading assembly 2200, according to an embodiment of the present subject matter. As described herein, the mandrel 2210 extends through the balloon socket 402 of the scoring device 100, and the scoring elements 110 surround the balloon socket 402. The scoring device 100 includes the distal portion 104, and the mandrel 2210 extends through the distal portion 104 of the scoring device 100 (e.g., through a distal tip socket, or the like).

Figure 25:
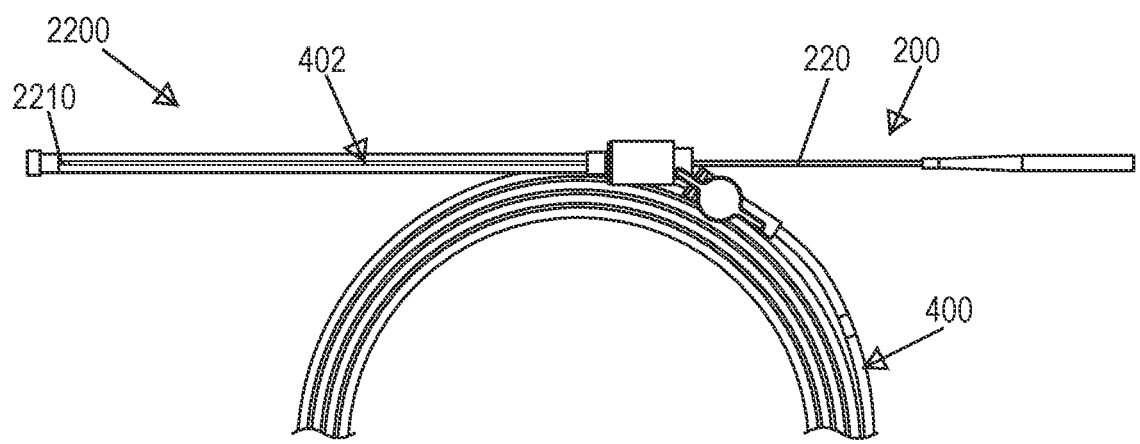
FIG. 25 illustrates the loading assembly including a catheter, according to an embodiment of the present subject matter
Figure 26:
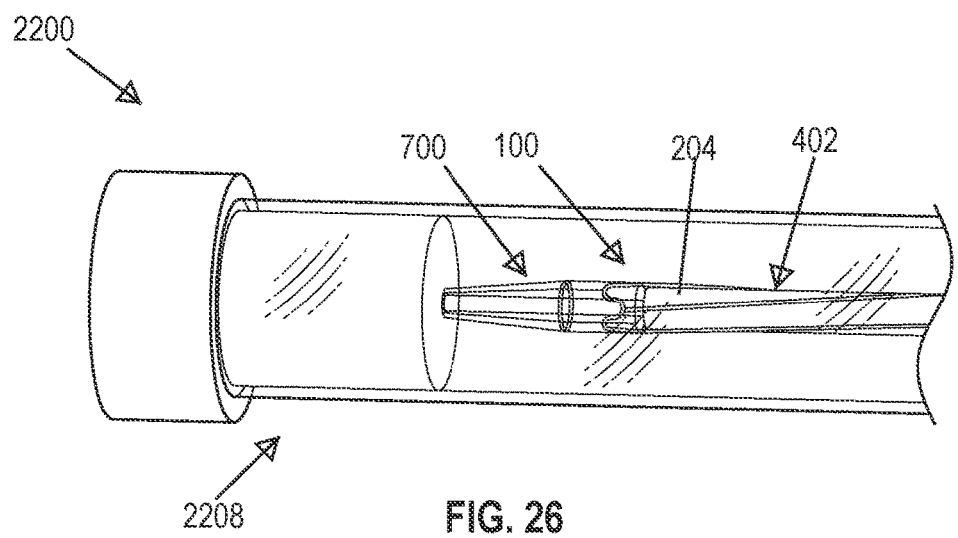
FIG. 26 illustrates the distal portion of the loading assembly, according to an embodiment of the present subject matter

FIG. 25 illustrates the loading assembly 2200 including the catheter 200, according to an embodiment of the present subject matter. For instance, the catheter 200 is loaded onto the mandrel 2210, and the mandrel 2210 facilitates assembly of the catheter with the scoring device 100. For instance, the mandrel 2210 guides the balloon 204 (shown in FIG. 26) of the catheter 200 through one or more of the catheter socket 400 or the balloon socket 402. Thus, the balloon optionally extends through the balloon socket 402 and the distal portion 214 of the catheter 200 is seated into the distal portion 104 of the scoring device 100 (e.g., the balloon 202 is engaged with the tapered portion 702 of the distal tip socket 700, shown in FIG. 7). FIG. 26 illustrates the distal portion 2208 of the loading assembly 2200, according to an embodiment of the present subject matter. The balloon 204 is optionally located in the balloon socket 402, and into the distal tip socket 700 of the scoring device 100.

Figure 27:
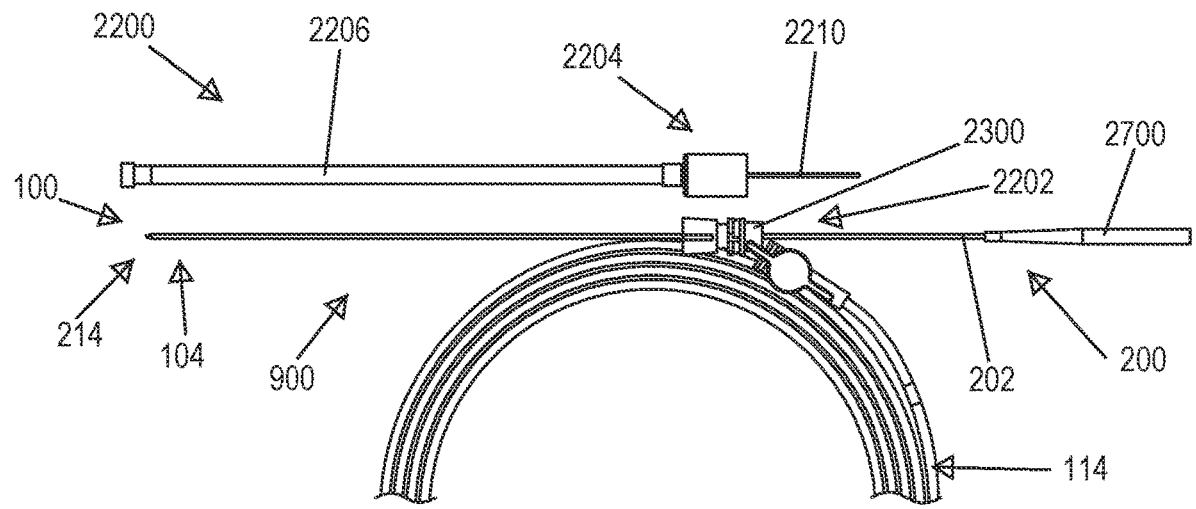
FIG. 27 illustrates a side view of an example of the loading assembly with a scoring tool sheath and an assembly interface separated from the assembly tool, according to an embodiment of the present subject matter.

FIG. 27 illustrates a side view of an example of the loading assembly 2200 with the scoring tool sheath 2206 and the assembly interface 2204 separated from the assembly tool 2202, according to an embodiment of the present subject matter. For instance, rotation of the assembly interface 2204 facilitates separation of one or more of the assembly interface 2204, the sheath 2206, or the mandrel 2210 from the assembly tool 2202. The catheter 200 optionally includes a hub 2700, and in some examples the hub is engaged with the loading interface 2300 (e.g., by pulling the catheter 200 through the assembly tool 2202). In another example, the catheter, such as the catheter shaft 202 and the hub 2700 are moved through the assembly tool 2202. For instance, the catheter 200 is loaded into the scoring device 100. The distal portions 104, 214 of the catheter 200 and the scoring device are moved (e.g., pushed, pulled, or the like) relative to the assembly tool 2202 and the retention sleeve 114 is biased over the catheter shaft 202 of catheter 200. Movement of the catheter assembly 900 relative to the assembly tool 2202 optionally engages the hub 2700 with the loading interface 2300 (shown in FIG. 30).

Figure 28:
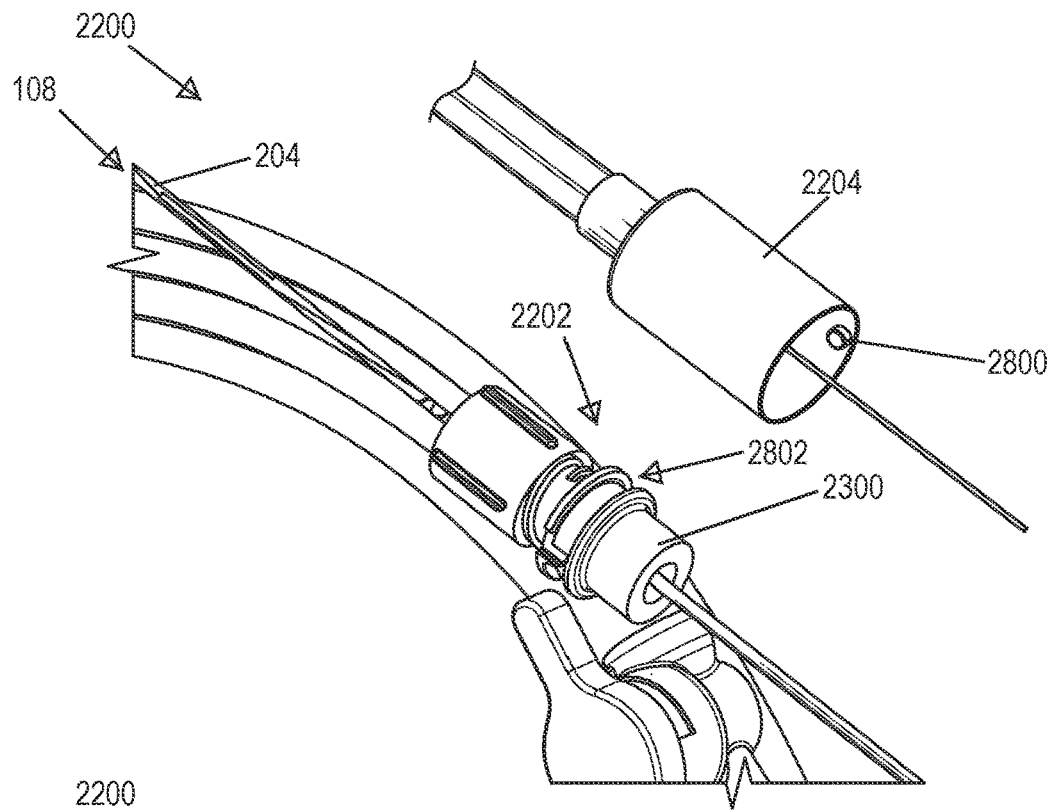
FIG. 28 illustrates a detailed perspective view of the loading assembly, according to an embodiment of the present subject matter.

FIG. 28 illustrates a detailed perspective view of the loading assembly 2200, according to an embodiment of the present subject matter. In an example, the assembly interface 2204 includes a locking feature 2800 that engages with the loading interface 2300 to attach the assembly interface 2204 with the assembly tool 2202. For instance, the assembly interface 2300 includes a socket 2802 that receives the locking feature 2800 to attach the assembly interface 2204 with the assembly tool 2202. In an example, rotation of the assembly interface 2204 disengages the locking feature 2800 from the socket 2802, for instance to facilitate separation of one or more of the assembly interface 2204, the sheath 2206, or the mandrel 2210 from the assembly tool 2202. FIG. 28 shows the catheter shaft 202 on a first (e.g., distal, or the like) side of the assembly tool 2202. Additionally, the balloon 204 is received in the balloon socket 402 on a second side of the scoring tool 108.

Figure 29:
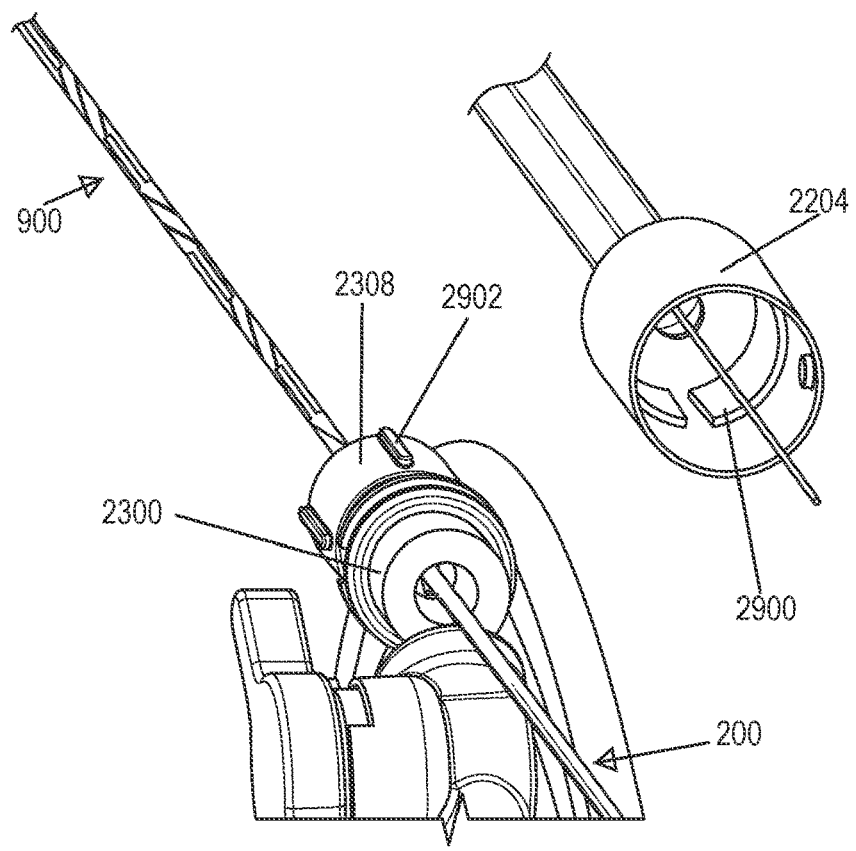
FIG. 29 illustrates another detailed perspective view of the loading assembly, according to an embodiment of the present subject matter.

FIG. 29 illustrates another detailed perspective view of the loading assembly 2200, according to an embodiment of the present subject matter. In an example, the assembly interface 2204 includes drive coupling features 2900, and the assembly drive 2308 includes corresponding interface coupling features 2902. The drive coupling features 2900 engage with the interface coupling features 2902, for example to facilitate displacement of the assembly drive 2308. In an example, rotation of the assembly interface 2204 correspondingly rotates the assembly drive 2308 because the drive coupling features 2900 are engaged with the interface coupling features 2902. Optionally, the assembly drive 2308 is threadingly engaged with the loading interface 2300, and rotation of the assembly drive 2308 displaces the assembly drive 2308 relative to the loading interface 2300. Accordingly, the loading assembly 2200 facilitates assembly of the catheter assembly 900, for instance by transitioning the retention sleeve 114 (shown in FIG. 27) and the catheter 200 from the decoupled configuration to the assembled configuration. In an example, the retention sleeve and catheter in the assembled configuration extend from the assembly fitting 2302.

Figure 30:
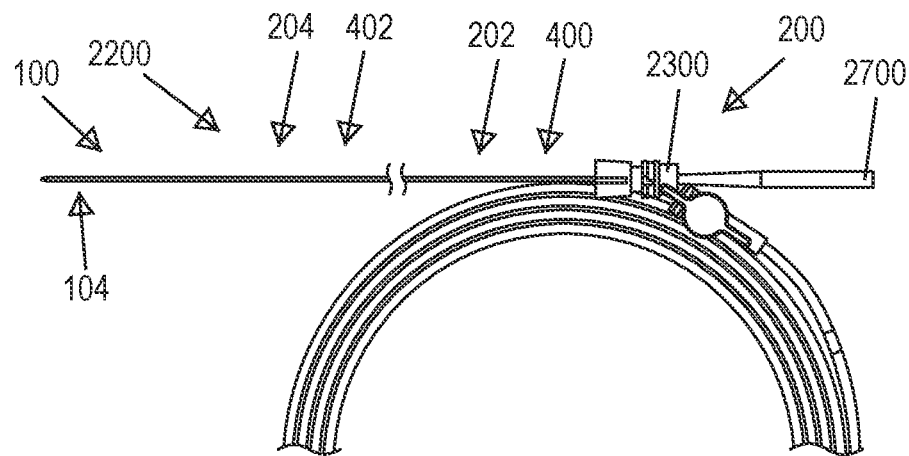
FIG. 30 illustrates another side view of the loading assembly including a catheter, according to an embodiment of the present subject matter.

FIG. 30 illustrates another side view of the loading assembly 2200 including the catheter 200, according to an embodiment of the present subject matter. In an example, the catheter 200 and the scoring device 100 are displaced relative to the assembly tool 2202 (e.g., by pulling the distal portion 104, or the like). In another example, the hub 2700 is engaged with the loading interface 2300 by displacing the scoring device 100 and the catheter 200 relative to the assembly tool 2202. In an example, displacing the scoring device 100 and the catheter 200 facilitates assembly of the retention sleeve 114 over the catheter 200, for instance by biasing the retention sleeve 114 over the catheter shaft 202. Thus, the loading assembly 2200 facilitates the selective reception of the balloon 204 within the balloon socket 200 (also shown in FIG. 14) and the selective reception of the catheter shaft 202 within the catheter socket 400 (also shown in FIG. 11).

Figure 31:
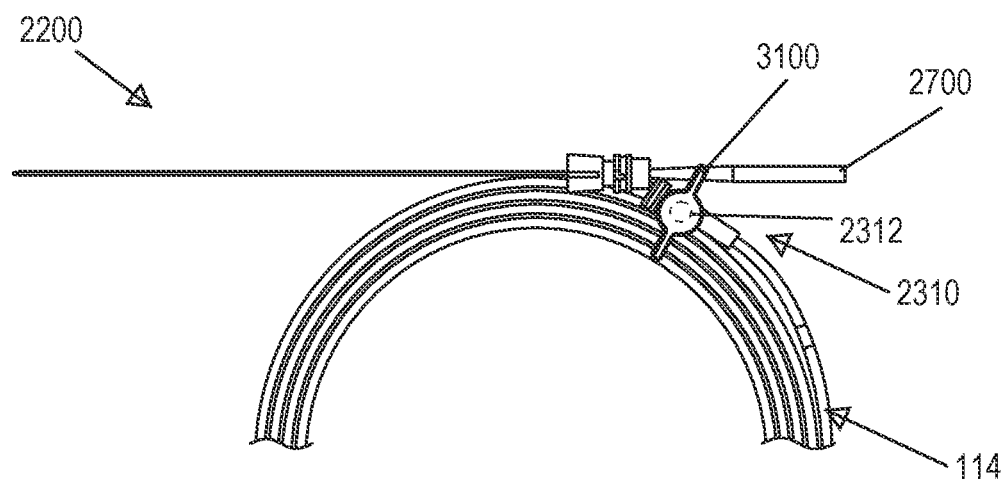
FIG. 31 illustrates a side view of the loading assembly including a cutter, according to an embodiment of the present subject matter.

FIG. 31 illustrates a side view of the loading assembly 2200 including the cutter 2310, according to an embodiment of the present subject matter. In an example, the cutter 2310 includes a cutting operator 3100 (e.g., a handle, lever, switch, or the like) that operates the cutter 2310 to sever the retention sleeve 114. For instance, the cutting operator 3100 is coupled with the sleeve cutting element 2312 (also shown in FIG. 32), and the cutting operator is rotated to correspondingly rotate the cutting element 2312. As described herein, rotation of the cutting element 2312 severs the retention sleeve 114. Accordingly, the cutter 2310 facilitates trimming of the retention sleeve 114, for instance to terminate the retention sleeve 114 proximate to the hub 2700. For example, the cutter 2310 allows the scoring device 100 to retain a plurality of catheters (with each of the catheters having a different profile, such as the catheters 200, 1200 shown respectively in FIGS. 2 and 12), for instance because the cutter 2310 allows the length of the retention sleeve 114 to be trimmed to correspond with a length of one or more of the plurality of catheters. Thus, in an example, the loading assembly 2200 facilitates transitioning of the catheter assembly 900 between the decoupled and assembled configurations, with the catheter assembly 900 including a plurality of catheters (with each of the catheters having a different profile).

Figure 32:
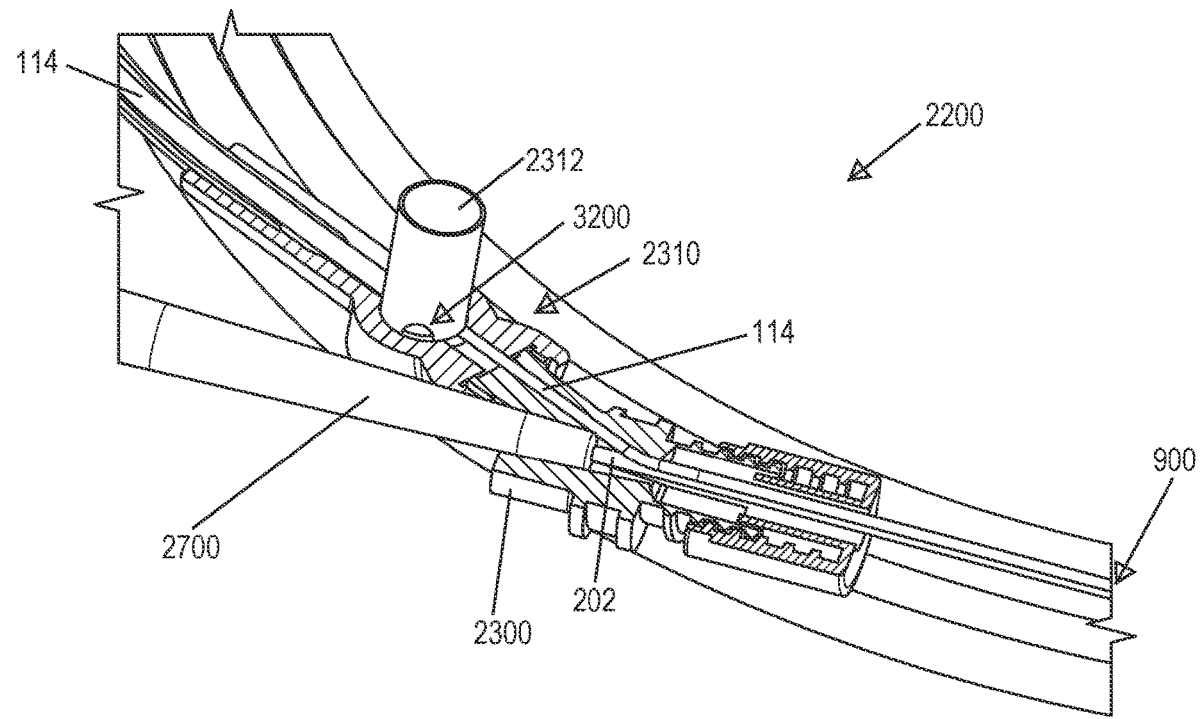
FIG. 32 illustrates a cross-sectional view of the loading assembly, according to an embodiment of the present subject matter.

FIG. 32 illustrates a cross-sectional view of the loading assembly 2200, according to an embodiment of the present subject matter. The loading assembly 2200 includes the cutter 2310, and the cutter 2310 includes the sleeve cutting element 2312. The sleeve cutting element 2312 includes a cutting orifice 3200. In the decoupled configuration, the retention sleeve 114 passes through the sleeve cutting element 2312. As described herein, the catheter assembly 900 includes a decoupled configuration and an assembled configuration. In the decoupled configuration, the retention sleeve 114 passes through the cutting orifice 3200 of the sleeve cutting element 2312. A user engages with the cutter 2310, for instance by engaging with the cutting operator 3100 (shown in FIG. 31) to rotate the sleeve cutting element 2312 relative to the sleeve cutting housing 2314. In an example, rotation of the sleeve cutting element 2312 severs the retention sleeve 114. For instance, the sleeve cutting element 2312 proximate the cutting orifice 3200 engages with the retention sleeve 114 to sever (e.g., cut, slice, chop, shear, or the like) the retention sleeve 114. Thus, in the assembled configuration, the sleeve cutting element 2312 severs the retention sleeve 114, for instance to trim the retention sleeve 114 to a specified length (e.g., to a retention sleeve length corresponding to a length of a catheter shaft). Accordingly, the retention sleeve 114 is severed proximate the catheter, for example to facilitate marriage of the retention sleeve 114 with the catheter shaft 202.

In an example, the hub 2700 of the catheter 200 is at least partially received by the loading interface 2300. For instance, the loading interface 2300 receives a portion of the hub to align the proximal portion of the catheter 200 relative to the proximal portion 102 of the scoring device 100. Accordingly, in the assembled configuration the catheter assembly 900 includes one or more components of the loading assembly 2200, for instance the loading interface 2300.

Figure 33:
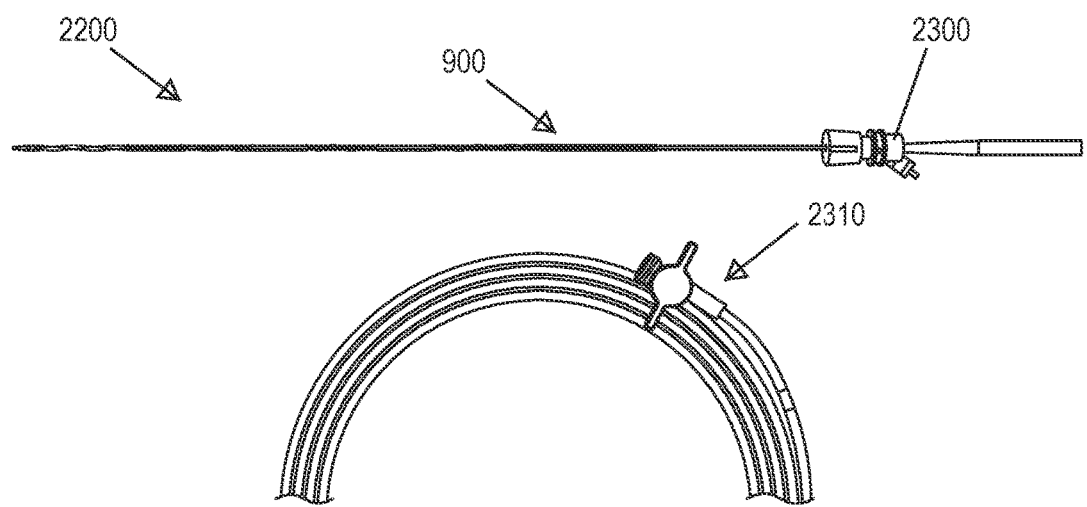
FIG. 33 illustrates yet another side view of the loading assembly, according to an embodiment of the present subject matter.
Figure 43:
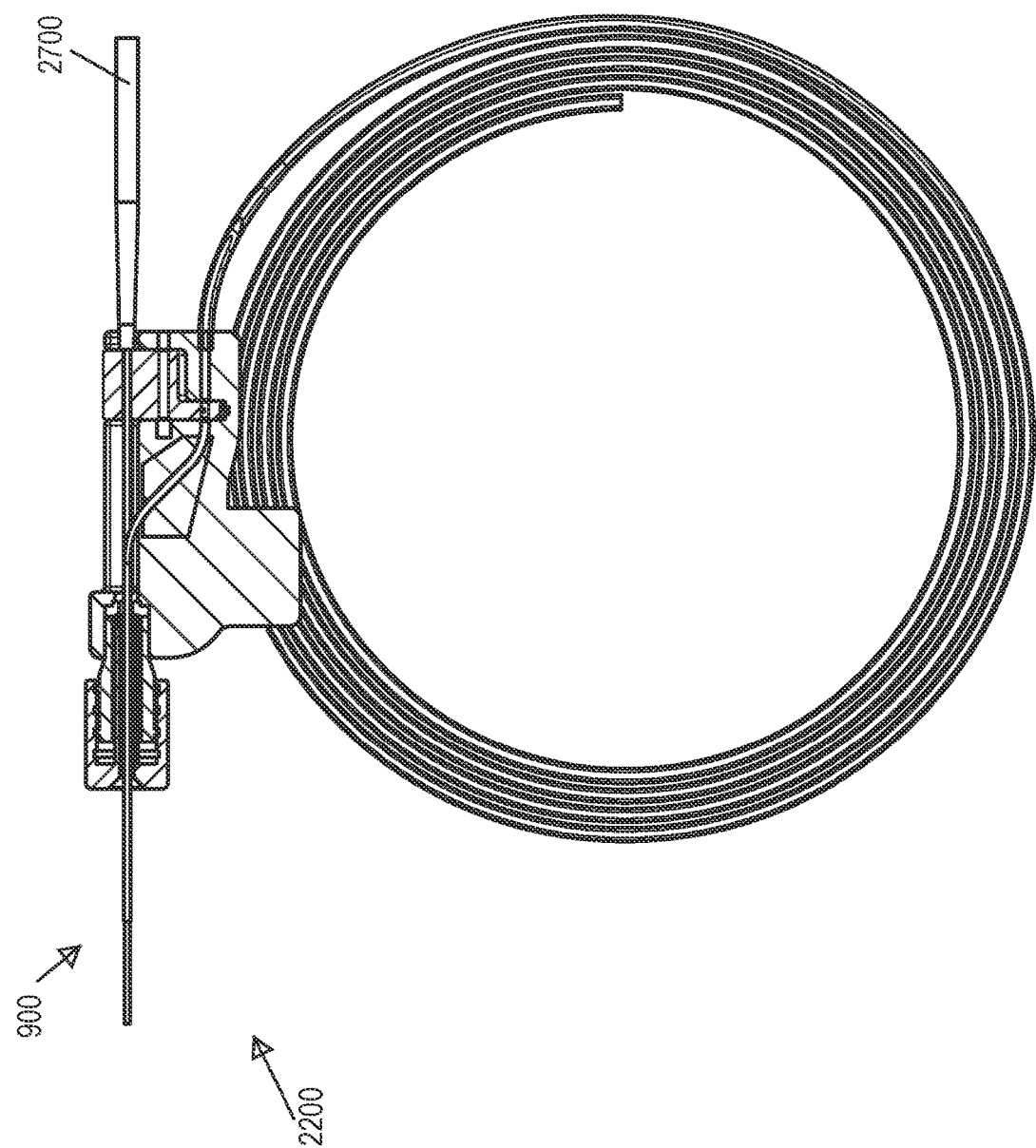
FIG. 43 illustrates another side view of the loading assembly of FIG. 34, according to an embodiment of the present subject matter.
Figure 44:
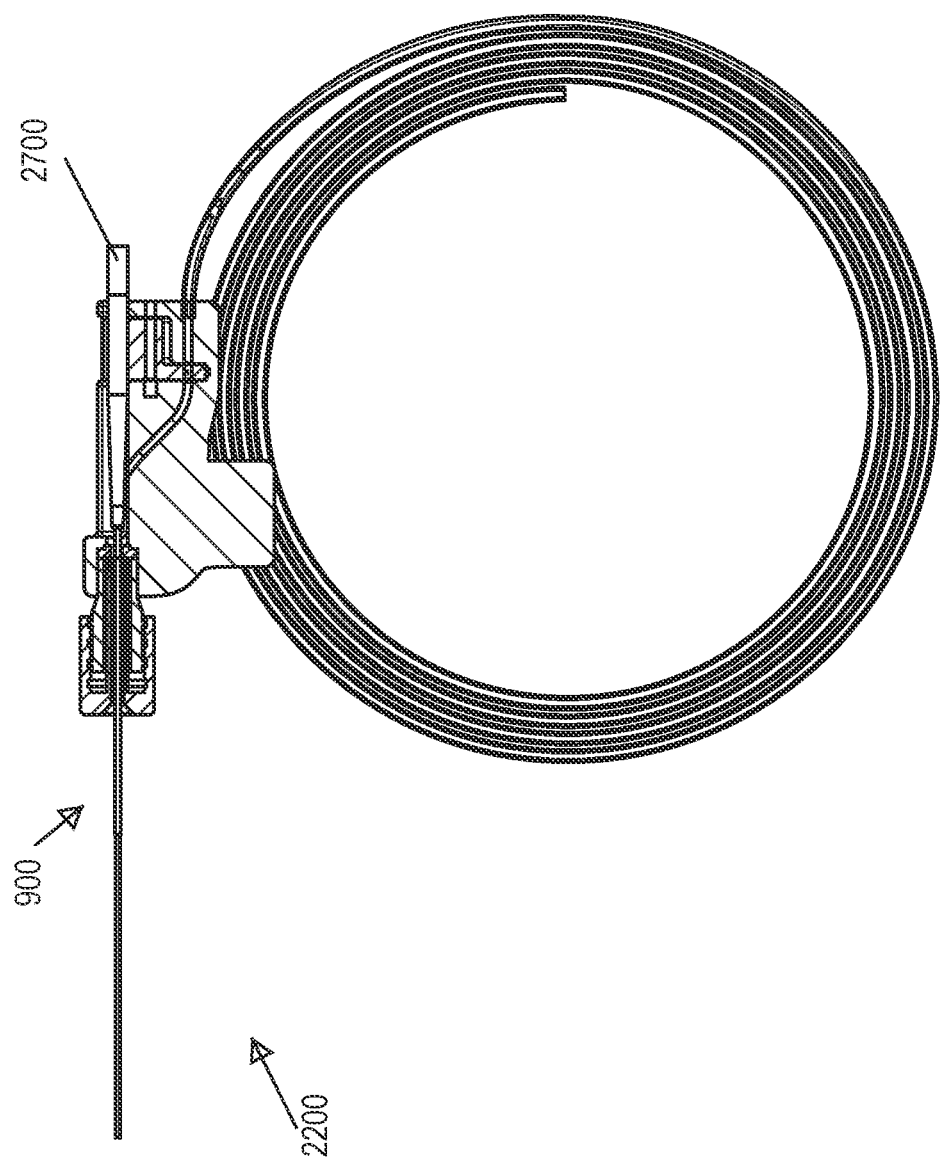
FIG. 44 illustrates yet a side view of the loading assembly of FIG. 34 with a catheter hub moved relative to a loading tool with a catheter assembly in an assembled configuration, according to an embodiment of the present subject matter.

FIG. 33 illustrates yet another side view of the loading assembly 2200, according to an embodiment of the present subject matter. In an example, one or more components of the loading assembly 2200 are separable from other ones of the components of the loading assembly 2200. For instance, in the assembled configuration the loading interface 2300 is separable from the cutter 2310. Accordingly, the cutter 2310 (or other components of the loading assembly 2200) are optionally discarded once the catheter assembly 900 is transitioned to the assembled configuration.

FIGS. 34-44 illustrate various views of another example of the loading assembly 2200. As described herein, the loading assembly 2200 includes one or more of the assembly tool 2202, assembly interface 2204, and the loading interface 2300, or the assembly fitting 2302. The loading assembly 2200 optionally includes the assembly drive 2308. In an example, the assembly interface 2204 receives each of the retention sleeve 114 and the catheter 200 in separated or partially separated conditions. For instance, the assembly interface 2204 facilitates assembly of the retention sleeve 114 over the catheter shaft 202.

In an example, the assembly interface 2204 is rotatably coupled relative to the assembly fitting 2300. In one example, the assembly interface 2204 is rotatably coupled with the loading interface 2300. The assembly fitting 2302 is received in the loading interface 2300, and rotation of the assembly interface 2204 compresses the assembly fitting 2302 with the loading interface 2300. For example, the assembly fitting 2302 is forced through the compression orifice 2306 of the loading interface 2300. The compression orifice 2306 includes a constriction (e.g., reduction in cross-sectional area, or the like) within the loading interface 2300, and forcing of the assembly fitting through the orifice 2306 compresses the assembly fitting 2302.

In one example, the loading interface 2300 facilitates transitioning of the catheter assembly 900 from the decoupled configuration to the assembled configuration. For instance, the loading interface 2300 biases the retention sleeve 114 over the catheter shaft 202. In another example, the assembly fitting 2302 guides the retention sleeve 114 onto catheter shaft 202 and loads the shaft 202 into the sleeve 114 similar to as discussed herein. In another example, the assembly interface 2204 is rotated relative to the drive 2308 and the interior (e.g., a barrel, or the like) of the assembly interface 2204 is driven toward an affixation seal, such as the collet 2304. In one example, the assembly fitting 2302 is the assembly interface 2204. In yet another example, longitudinal compression of the assembly interface 2302 (or the collet 2304) causes inward compression of the assembly interface 2302, and corresponding compression of the retention sleeve 114 and the catheter 200. Two or more of these fitting assembly examples can work together to ensure the seating of the catheter shaft 202 in the retention sleeve 114. Accordingly, the loading assembly 2200 facilitates transitioning of the catheter assembly 900 from the decoupled configuration to the assembled configuration.

Figure 45:
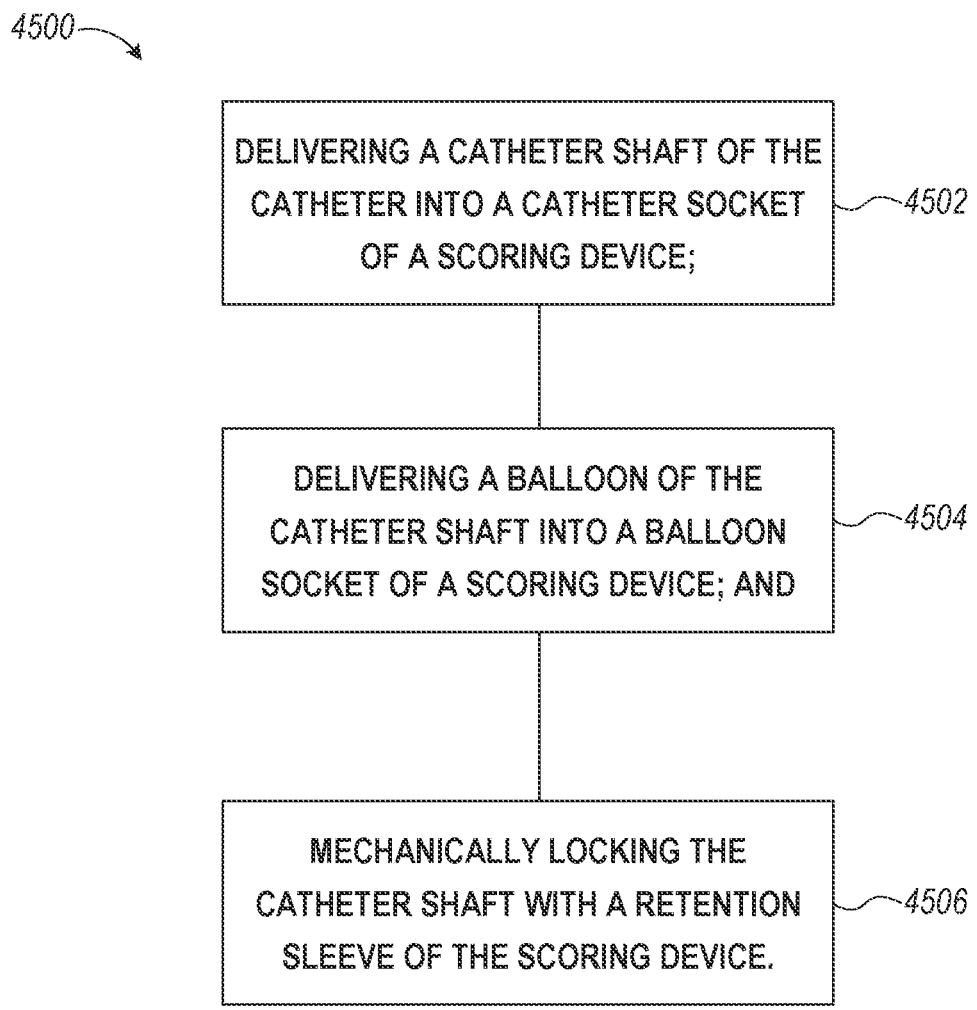
FIG. 45 illustrates a diagram of a method for assembling a scoring device to a catheter, including one or more of the scoring device or the catheters described herein, according to an embodiment of the present subject matter.

FIG. 45 illustrates a diagram of a method 4500 for assembling a scoring device to a catheter, including one or more of the scoring device 100 or the catheters 200, 1200 described herein. In describing the method 4500, reference is made to one or more components, features, functions and operations previously described herein. Where convenient, reference is made to the components, features, operations and the like with reference numerals. The reference numerals provided are exemplary and are not exclusive. For instance, components, features, functions, operations and the like described in the method 4500 include, but are not limited to, the corresponding numbered elements provided herein and other corresponding elements described herein (both numbered and unnumbered) as well as their equivalents.

At 4502, the method 4500 includes delivering a catheter shaft 202 of the catheter 200 into a catheter socket 400 of a scoring device 100. At 4504, the method 4500 includes delivering a balloon 204 of the catheter shaft 202 into a balloon socket 402 of the scoring device 100. At 4506, the method 4500 includes mechanically locking the catheter shaft 202 with a retention sleeve 114 of the scoring device 100.

Several options for the method 1800 follow. For instance, a force is optionally applied to the catheter shaft 202 to deliver the catheter shaft 202 into the balloon socket 402. In another example, delivering the catheter shaft 202 into the catheter socket 400 includes delivering the catheter shaft 202 through a catheter port 500. For instance, the catheter port 500 is in communication with the catheter socket 400 to facilitate reception of the catheter 200 by the scoring device 100. The method 4500 optionally includes expanding the scoring array 100 with the balloon 204 of the catheter 200 (e.g., between deflated and inflated configurations). In yet another example, mechanically locking the catheter shaft 202 with the retention sleeve 114 includes biasing the retention sleeve 114 over the catheter shaft 202. For instance, biasing the retention sleeve 114 over the catheter shaft 202 includes delivering each of the retention sleeve 114 and the catheter shaft 202 into an assembly fitting, for instance the assembly fitting 2304 of the loading assembly 2200. The assembly fitting 2304 optionally biases the catheter shaft into the catheter socket through a catheter port.

Various Notes & Aspects

Example 1 is a scoring device configured for retention of a catheter shaft, the scoring device comprising: a proximal portion; a distal portion, including a distal tip; a retention sleeve extending between the proximal and distal portions, the retention sleeve having a catheter socket configured to selectively receive and mechanically engage the catheter shaft; and a scoring tool coupled with the retention sleeve proximate to the distal portion, the scoring tool including: a balloon socket configured to selectively receive a balloon of the catheter shaft; and one or more scoring elements extending around the balloon socket, the one or more scoring elements configured to provide localized scoring to vasculature.

In Example 2, the subject matter of Example 1 optionally includes a deformable catheter port included in the retention sleeve, wherein: the catheter port is in communication with the catheter socket; and the catheter port is elastically deformable and configured to receive the catheter shaft.

In Example 3, the subject matter of Example 2 optionally includes wherein: the retention sleeve includes first and second opposed faces extending between the proximal and distal portions; and the deformable catheter port includes a slot extending along the first and second opposed faces.

In Example 4, the subject matter of any one or more of Examples 2-3 optionally include wherein: the retention sleeve is configured to elastically deform, and the elastic deformation of the retention sleeve varies a socket profile of the catheter socket; and elastic deformation of the retention sleeve varies a characteristic of the catheter port to facilitate passage of the catheter shaft through the catheter port.

In Example 5, the subject matter of any one or more of Examples 2-4 optionally include wherein: the retention sleeve extends arcuately from a first face to a second face; the catheter port is located between the first face and the second face; and the retention sleeve includes an initial configuration and a loading configuration, wherein: in the initial configuration, the first face is proximate the second face; and in the loading configuration, the first face and second face are deformed apart relative to the initial configuration for reception of the catheter shaft.

In Example 6, the subject matter of any one or more of Examples 1-5 optionally include wherein the retention sleeve is elastically deformable, and elastic deformation of the retention sleeve varies a volume of the catheter socket.

In Example 7, the subject matter of any one or more of Examples 1-6 optionally include wherein the distal portion includes a distal tip socket configured to seat a catheter shaft distal portion.

In Example 8, the subject matter of Example 7 optionally includes wherein the distal tip socket includes a mandrel lumen configured to pass a mandrel through the distal tip socket.

In Example 9, the subject matter of any one or more of Examples 7-8 optionally include wherein the distal tip socket includes: a tapered portion configured to receive distal coupling features of the catheter shaft distal portion; and wherein reception of the distal coupling features aligns the catheter shaft distal portion relative to the distal tip socket and seats the catheter shaft distal portion within the distal tip socket.

In Example 10, the subject matter of any one or more of Examples 1-9 optionally include the catheter shaft received in the catheter socket.

In Example 11, the subject matter of Example 10 optionally includes wherein the balloon of the catheter shaft extends through the balloon socket of the scoring tool, and the catheter shaft distal portion is seated with the distal tip socket.

In Example 12, the subject matter of any one or more of Examples 10-11 optionally include wherein the mechanical engagement of the catheter socket with the catheter shaft constrains relative movement between the catheter shaft and the retention sleeve.

In Example 13, the subject matter of Example 12 optionally includes wherein relative movement includes lateral movement of the catheter shaft along a longitudinal axis of the retention sleeve.

In Example 14, the subject matter of any one or more of Examples 12-13 optionally include wherein relative movement includes rotational movement of the catheter shaft about a longitudinal axis of the retention sleeve.

In Example 15, the subject matter of any one or more of Examples 12-14 optionally include wherein the mechanical engagement of the catheter socket includes the retention sleeve grasping the catheter shaft.

In Example 16, the subject matter of any one or more of Examples 1-15 optionally include wherein the scoring tool includes an initial configuration and an expanded configuration, wherein: in the initial configuration the scoring tool has a first tool profile; and in the expanded configuration the scoring tool has a second tool profile, the second tool profile larger than the first tool profile.

In Example 17, the subject matter of Example 16 optionally includes the balloon located in the balloon socket, wherein: the balloon is configured to expand between a deflated configuration and an inflated configuration, and wherein: in the deflated configuration, the balloon has a first balloon profile and the scoring tool has the first tool profile; and in the inflated configuration: the balloon has a second balloon profile larger than the first balloon profile; and the scoring tool has the second tool profile.

In Example 18, the subject matter of any one or more of Examples 1-17 optionally include wherein the scoring tool is configured to expand outward in conformity with expansion of the balloon located in the balloon socket.

In Example 19, the subject matter of any one or more of Examples 1-18 optionally include wherein the one or more scoring elements are included in a scoring array having two or more of the scoring elements.

In Example 20, the subject matter of Example 19 optionally includes wherein: the scoring array has a first scoring section with a first scoring element profile; and the scoring array has a second scoring section with a second scoring element profile, the second scoring element profile different than the first scoring element profile.

In Example 21, the subject matter of Example 20 optionally includes wherein the first cutting scoring profile includes a first scoring element having an elongated profile.

In Example 22, the subject matter of Example 21 optionally includes wherein the second scoring element profile includes a second scoring element having a helical profile.

In Example 23, the subject matter of Example 22 optionally includes wherein the first scoring element is coupled with the second scoring element.

In Example 24, the subject matter of Example 23 optionally includes a third scoring section having a third scoring element profile, the third scoring element profile including a third scoring element, wherein the third scoring element is coupled with the second scoring element.

In Example 25, the subject matter of any one or more of Examples 23-24 optionally include wherein the third scoring element has the elliptical profile.

In Example 26, the subject matter of any one or more of Examples 23-25 optionally include wherein: the first scoring element is coupled with a first end of the second scoring element; and the third scoring element is coupled with a second end of the second scoring element.

In Example 27, the subject matter of any one or more of Examples 20-26 optionally include wherein the first scoring element profile includes a first scoring element having a helical profile.

In Example 28, the subject matter of any one or more of Examples 1-27 optionally include wherein the retention sleeve has a C-shaped cross-section.

In Example 29, the subject matter of any one or more of Examples 1-28 optionally include wherein the scoring device includes an expansion region having one or more expansion ribbons configured to expand in conformance with the balloon in the balloon socket.

Example 30 is a catheter assembly, comprising: a first balloon catheter, including: a first catheter shaft; a first balloon coupled with the first catheter shaft, wherein the first balloon is expandable between deflated configuration and an inflated configuration; a scoring device configured for retention of the first catheter shaft, the scoring device including: a proximal portion; a distal portion, including a distal tip; a retention sleeve extending between the proximal and distal portions, the retention sleeve having a catheter socket configured to selectively receive and mechanically engage the first catheter shaft; a scoring tool coupled with the retention sleeve proximate to the distal portion, the scoring tool including: a balloon socket configured to selectively receive the first balloon; and one or more scoring elements extending around the balloon socket, the one or more scoring elements configured to provide localized scoring to vasculature.

In Example 31, the subject matter of Example 30 optionally includes wherein the first balloon catheter has a first profile; and the catheter assembly includes a second balloon catheter having a second profile, the second profile different than the first profile, wherein the second balloon catheter includes: a second catheter shaft; and a second balloon; the retention sleeve is configured to interchangeably retain the first catheter shaft or the second catheter shaft; and the balloon socket is configured to interchangeably receive the first balloon with the first catheter shaft retained in the retention sleeve or interchangeably receive the second balloon with the second catheter shaft retained in the retention sleeve.

In Example 32, the subject matter of Example 31 optionally includes wherein: the first catheter shaft has a first length; the second catheter shaft has a second length, the second length different than the first length; and the first balloon has a first initial volume.

In Example 33, the subject matter of Example 32 optionally includes wherein the second balloon has the first initial volume.

In Example 34, the subject matter of Example 33 optionally includes wherein: the first balloon has a first expanded volume; the second balloon has a second expanded volume, the second expanded volume different than the first expanded volume.

In Example 35, the subject matter of any one or more of Examples 32-34 optionally include wherein the second balloon has a second initial volume, the second initial volume different than the first initial volume.

In Example 36, the subject matter of any one or more of Examples 31-35 optionally include wherein: the balloon has a first initial volume; the second balloon has a second initial volume, the second initial volume different than the first initial volume; and the first catheter shaft has a first length.

In Example 37, the subject matter of Example 36 optionally includes wherein the second catheter shaft has the first length.

In Example 38, the subject matter of Example 37 optionally includes wherein the second catheter shaft has a second length, the second length different than the first length.

In Example 39, the subject matter of any one or more of Examples 30-38 optionally include wherein the scoring device includes an expansion region having one or more expansion ribbons configured to expand in conformance with the first balloon in the balloon socket.

In Example 40, the subject matter of Example 39 optionally includes wherein the one or more expansion ribbons extend helically around the balloon socket.

In Example 41, the subject matter of any one or more of Examples 39-40 optionally include wherein the one or more expansion ribbons includes a plurality of expansion ribbons, and each of the expansion ribbons are isolated from each other.

Example 42 is a loading assembly comprising: a scoring device configured for assembly with a balloon catheter, the scoring device includes: a retention sleeve extending from a proximal portion to a distal portion; and a scoring tool coupled with the retention sleeve, the scoring tool includes a balloon socket and one or more scoring elements; an assembly tool configured to assemble the scoring device to the balloon catheter, the assembly tool includes: an assembly fitting configured to receive each of the retention sleeve and the balloon catheter in a decoupled configuration and assemble the retention sleeve over the balloon catheter in an assembled configuration; and a sleeve cutting element coupled with the assembly tool, the sleeve cutting element is configured to cut the retention sleeve.

In Example 43, the subject matter of Example 42 optionally includes wherein in the decoupled configuration a balloon of the balloon catheter is received within the balloon socket of the scoring tool.

In Example 44, the subject matter of any one or more of Examples 42-43 optionally include wherein the assembly fitting includes an assembly collet extending around the retention sleeve and the balloon catheter.

In Example 45, the subject matter of Example 44 optionally includes wherein the assembly tool includes: an assembly interface rotatably coupled relative to the assembly fitting, and rotation of the assembly interface compresses the assembly collet and assembles the retention sleeve over the balloon catheter.

In Example 46, the subject matter of Example 45 optionally includes wherein the assembly tool includes a loading interface, the assembly interface is rotatably coupled with the loading interface, and the assembly collet is coupled with the loading interface.

In Example 47, the subject matter of any one or more of Examples 42-46 optionally include wherein the retention sleeve includes a catheter port, and the balloon catheter is assembled to the retention sleeve through the catheter port.

In Example 48, the subject matter of Example 47 optionally includes wherein the retention sleeve has an arcuate cross section interrupted with the catheter port, and the catheter port is an elongate slot extending between the proximal portion and the distal portion.

In Example 49, the subject matter of Example 48 optionally includes wherein the assembly fitting is configured to bias the retention sleeve over the balloon catheter and open the elongate slot for reception of the balloon catheter within the retention sleeve.

In Example 50, the subject matter of any one or more of Examples 42-49 optionally include wherein the sleeve cutting element is positioned along the retention sleeve; in the decoupled configuration the retention sleeve passes through the sleeve cutting element; and in the assembled configuration the sleeve cutting element severs the retention sleeve.

In Example 51, the subject matter of any one or more of Examples 42-50 optionally include a scoring tool sheath surrounding the scoring tool and coupled with the assembly tool.

In Example 52, the subject matter of Example 51 optionally includes a catheter loading mandrel coupled with the scoring tool sheath and extending through the assembly tool; in the decoupled configuration the catheter loading mandrel extends into the balloon catheter, and the balloon socket of the scoring tool receives the balloon of the balloon catheter; and in the assembled configuration the scoring tool sheath and the catheter loading mandrel are decoupled from the scoring tool, the balloon, and the assembled retention sleeve and balloon catheter.

In Example 53, the subject matter of any one or more of Examples 42-52 optionally include the balloon catheter.

Example 54 is a loading assembly comprising: a scoring device configured for assembly with a balloon catheter, the scoring device includes: a retention sleeve extending from a proximal portion to a distal portion; and a scoring tool coupled with the retention sleeve, the scoring tool includes a balloon socket and one or more scoring elements; an assembly tool configured to assemble the scoring device to the balloon catheter, the assembly tool includes: an assembly fitting configured to transition the retention sleeve and the balloon catheter from a decoupled configured to an assembled configuration; in the decoupled configuration a balloon of the balloon catheter is received in the balloon socket of the scoring tool, and the retention sleeve and the balloon catheter are decoupled and movably received at the assembly fitting; and in the assembled configuration the assembly fitting biases the retention sleeve over the balloon catheter, and the assembled retention sleeve over the balloon catheter extends from the assembly fitting.

In Example 55, the subject matter of Example 54 optionally includes wherein the assembly fitting includes an assembly collet extending around the retention sleeve and the balloon catheter.

In Example 56, the subject matter of Example 55 optionally includes wherein the assembly tool includes: an assembly interface rotatably coupled relative to the assembly fitting, and rotation of the assembly interface compresses the assembly collet and the compressed assembly collet biases the retention sleeve over the balloon catheter.

In Example 57, the subject matter of Example 56 optionally includes wherein the assembly tool includes a loading interface, the assembly interface is rotatably coupled with the loading interface, and the assembly collet is coupled with the loading interface.

In Example 58, the subject matter of any one or more of Examples 54-57 optionally include wherein the retention sleeve includes a catheter port, and the balloon catheter is assembled to the retention sleeve through the catheter port.

In Example 59, the subject matter of Example 58 optionally includes wherein the retention sleeve has an arcuate cross section interrupted with the catheter port, and the catheter port is an elongate slot extending between the proximal portion and the distal portion.

In Example 60, the subject matter of Example 59 optionally includes wherein the assembly fitting is configured to bias the retention sleeve over the balloon catheter and open the elongate slot for reception of the balloon catheter within the retention sleeve.

In Example 61, the subject matter of any one or more of Examples 54-60 optionally include wherein the assembly tool includes a sleeve cutting element positioned along the retention sleeve; in the decoupled configuration the retention sleeve passes through the sleeve cutting element; and in the assembled configuration the sleeve cutting element severs the retention sleeve proximate to the balloon catheter.

In Example 62, the subject matter of Example 61 optionally includes wherein the sleeve cutting element includes a sleeve port, and in the decoupled configuration the retention sleeve passes through the sleeve port.

In Example 63, the subject matter of any one or more of Examples 54-62 optionally include a scoring tool sheath surrounding the scoring tool and extending from the assembly tool.

In Example 64, the subject matter of Example 63 optionally includes a catheter loading mandrel coupled with the scoring tool sheath and extending through the assembly tool, the catheter loading mandrel configured to guide the balloon of the balloon catheter through the assembly tool and into the balloon socket of the scoring tool.

In Example 65, the subject matter of Example 64 optionally includes the balloon catheter.

Example 66 is a method for assembling a scoring device to a catheter, comprising: delivering a catheter shaft of the catheter into a catheter socket of a scoring device; delivering a balloon of the catheter shaft into a balloon socket of a scoring device; mechanically locking the catheter shaft with a retention sleeve of the scoring device.

In Example 67, the subject matter of Example 66 optionally includes applying a force to catheter shaft.

In Example 68, the subject matter of any one or more of Examples 66-67 optionally include wherein delivering the catheter shaft into the catheter socket includes delivering the catheter shaft through a catheter port, the catheter port in communication with the catheter socket.

In Example 69, the subject matter of any one or more of Examples 66-68 optionally include expanding the scoring array with the balloon of the catheter 69 is In example 70, the subject matter of any one or more of Examples 66-69 optionally include wherein mechanically locking the catheter shaft with the retention sleeve includes biasing the retention sleeve over the catheter shaft, biasing the retention sleeve including: delivering each of the retention sleeve and the catheter shaft into an assembly fitting that biases the catheter shaft into the catheter socket through a catheter port.

Example 71 may include or use, or may optionally be combined with any portion or combination of any portions of any one or more of Examples 1-70 to include or use, subject matter that may include means for performing any one or more of the functions of Examples 1-70, or a machine-readable medium including instructions that, when performed by a machine, cause the machine to perform any one or more of the functions of Examples 1-70.

Each of these non-limiting examples can stand on its own, or can be combined in various permutations or combinations with one or more of the other examples.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with The claimed invention is:

1. A system including a scoring device configured for retention of a catheter shaft of a catheter, the system comprising:
the catheter shaft extending from a distal end to a proximal end, wherein the distal end has an inflatable balloon and the proximal end has a hub configured to operate the catheter;
the scoring device, including:
a proximal portion;
a distal portion, including a distal tip;
a retention sleeve extending between the proximal and distal portions, the retention sleeve having a catheter socket configured to selectively receive and mechanically engage the catheter shaft, and the retention sleeve is configured to extend from a shaft distal end to proximate the hub of the catheter shaft; and
a scoring tool coupled with the retention sleeve proximate to the distal portion and located distally with respect to the retention sleeve, the scoring tool including:
a balloon socket configured to selectively receive the balloon of the catheter shaft; and
one or more scoring elements extending around the balloon socket, the one or more scoring elements configured to provide localized scoring to vasculature.

2. The system of claim 1, further comprising a deformable catheter port included in the retention sleeve, wherein:
the catheter port is in communication with the catheter socket; and
the catheter port is elastically deformable and configured to receive the catheter shaft.

3. The system of claim 2, wherein:
the retention sleeve includes first and second opposed faces extending between the proximal and distal portions; and
the deformable catheter port includes a slot extending along the first and second opposed faces.

4. The system of claim 2, wherein:
the retention sleeve is configured to elastically deform, and the elastic deformation of the retention sleeve varies a socket profile of the catheter socket; and
elastic deformation of the retention sleeve varies a characteristic of the catheter port to facilitate passage of the catheter shaft through the catheter port.

5. The system of claim 2, wherein:
the retention sleeve extends arcuately from a first face to a second face;
the catheter port is located between the first face and the second face; and
the retention sleeve includes an initial configuration and a loading configuration wherein:
in the initial configuration, the first face is proximate the second face; and
in the loading configuration, the first face and second face are deformed apart relative to the initial configuration for reception of the catheter shaft.

6. The system of claim 2, wherein the deformable catheter port extends along the retention sleeve in correspondence with the retention sleeve length from the proximal to the distal portions.

7. The system of claim 1, wherein the distal portion includes a distal tip socket configured to seat a catheter shaft distal portion.

8. The system of claim 7, wherein the distal tip socket includes a mandrel lumen configured to pass a mandrel through the distal tip socket.

9. The system of claim 7, wherein the distal tip socket includes:
a tapered portion configured to receive distal coupling features of the catheter shaft distal portion; and
wherein reception of the distal coupling features aligns the catheter shaft distal portion relative to the distal tip socket and seats the catheter shaft distal portion within the distal tip socket.

10. The system of claim 1, wherein the balloon of the catheter shaft extends through the balloon socket of the scoring tool, and the catheter shaft distal portion is seated with the distal tip socket.

11. The scoring device of claim 1, wherein the mechanical engagement of the catheter socket with the catheter shaft statically secures the retention sleeve to the catheter shaft to constrain longitudinal movement of the catheter shaft along a longitudinal axis of the retention sleeve.

12. The system of claim 1, wherein relative movement includes lateral movement of the catheter shaft along a longitudinal axis of the retention sleeve.

13. The system of claim 1, wherein relative movement includes rotational movement of the catheter shaft about a longitudinal axis of the retention sleeve.

14. The system of claim 1, wherein the mechanical engagement of the catheter socket includes the retention sleeve grasping the catheter shaft.

15. The system of claim 1, wherein the scoring tool includes an initial configuration and an expanded configuration, wherein:
in the initial configuration the scoring tool has a first tool profile; and
in the expanded configuration the scoring tool has a second tool profile, the second tool profile larger than the first tool profile.

16. The system of claim 15, further comprising the balloon located in the balloon socket, wherein:
the balloon is configured to expand between a deflated configuration and an inflated configuration, and wherein:
in the deflated configuration, the balloon has a first balloon profile and the scoring tool has the first tool profile; and
in the inflated configuration:
the balloon has a second balloon profile larger than the first balloon profile; and
the scoring tool has the second tool profile.

17. The system of claim 1, wherein the scoring tool is configured to expand outward in conformity with expansion of the balloon located in the balloon socket.

18. The system of claim 1, wherein the distal portion of the retention sleeve has a tapered profile that facilitates loading of the catheter shaft into the retention sleeve.

19. The system of claim 1, wherein the retention sleeve has a C-shaped cross-section.

20. The system of claim 1, wherein the scoring device includes an expansion region having one or more expansion ribbons configured to axially expand in conformance with the balloon in the balloon socket.

21. A system including a scoring device configured for retention of a catheter shaft of a catheter, the system comprising:

the catheter shaft extending from a distal end to a proximal end, wherein the distal end has an inflatable balloon and the proximal end has a hub that operates the catheter;

the scoring device, including:
- a proximal portion;
- a distal portion, including a distal tip;
- a retention sleeve extending between the proximal and distal portions, the retention sleeve having a catheter socket configured to selectively receive and mechanically engage the catheter shaft, and the retention sleeve is configured to extend from a shaft distal end to proximate to a hub of the catheter shaft;
- a scoring tool coupled with the retention sleeve proximate to the distal portion and located distally with respect to the retention sleeve, the scoring tool including:
  - a balloon socket configured to selectively receive the balloon of the catheter shaft; and
  - one or more scoring elements extending around the balloon socket, the one or more scoring elements configured to provide localized scoring to vasculature; and
- wherein the catheter shaft is received in the catheter socket, and mechanical engagement of the catheter socket with the catheter shaft statically secures the retention sleeve to the catheter shaft to constrain longitudinal movement of the catheter shaft along a longitudinal axis of the retention sleeve.

22. The system of claim 21, further comprising a deformable catheter port included in the retention sleeve, wherein:
the catheter port is in communication with the catheter socket; and
the catheter port is elastically deformable and configured to receive the catheter shaft.

23. The system of claim 22, wherein:
the retention sleeve includes first and second opposed faces extending between the proximal and distal portions; and
the deformable catheter port includes a slot extending along the first and second opposed faces.

24. The system of claim 22, wherein:
the retention sleeve is configured to elastically deform, and the elastic deformation of the retention sleeve varies a socket profile of the catheter socket; and
elastic deformation of the retention sleeve varies a characteristic of the catheter port to facilitate passage of the catheter shaft through the catheter port.

25. The system of claim 22, wherein:
the retention sleeve extends arcuately from a first face to a second face;
the catheter port is located between the first face and the second face; and
the retention sleeve includes an initial configuration and a loading configuration wherein:
in the initial configuration, the first face is proximate the second face; and
in the loading configuration, the first face and second face are deformed apart relative to the initial configuration for reception of the catheter shaft.

26. The system of claim 22, wherein the deformable catheter port extends along the retention sleeve in correspondence with the retention sleeve length from the proximal to the distal portions.

27. The system of claim 21, wherein the distal portion includes a distal tip socket configured to seat a catheter shaft distal portion.

* * * * *